(12) United States Patent
Centen et al.

(10) Patent No.: US 11,197,628 B2
(45) Date of Patent: Dec. 14, 2021

(54) CARDIOVASCULAR HEALTH MONITORING DEVICE

(71) Applicant: Bodyport Inc., San Francisco, CA (US)

(72) Inventors: Corey James Centen, San Francisco, CA (US); Sarah Ann Smith, San Francisco, CA (US); Michael Prichard, Carlisle, MA (US)

(73) Assignee: Bodyport Inc., San Francisco, CA (US)

( * ) Notice: Subject to any disclaimer, the term of this patent is extended or adjusted under 35 U.S.C. 154(b) by 140 days.

(21) Appl. No.: 16/163,354

(22) Filed: Oct. 17, 2018

(65) Prior Publication Data

US 2019/0059761 A1 Feb. 28, 2019

Related U.S. Application Data

(63) Continuation-in-part of application No. 15/743,154, filed as application No. PCT/CA2015/051120 on Nov. 2, 2015.

(Continued)

(51) Int. Cl.
*A61B 5/25* (2021.01)
*A61B 5/00* (2006.01)
(Continued)

(52) U.S. Cl.
CPC .............. *A61B 5/25* (2021.01); *A61B 5/0535* (2013.01); *A61B 5/6829* (2013.01);
(Continued)

(58) Field of Classification Search
None
See application file for complete search history.

(56) References Cited

U.S. PATENT DOCUMENTS

| | | |
|---|---|---|
| 5,211,177 A | 5/1993 | Chesney et al. |
| 5,410,471 A | 4/1995 | Alyfuku et al. |

(Continued)

FOREIGN PATENT DOCUMENTS

| | | |
|---|---|---|
| CA | 2605239 A1 | 11/2006 |
| CA | 2882453 A1 | 3/2014 |

(Continued)

OTHER PUBLICATIONS

PCT International Search Report and Written Opinion. PCT Application No. PCT/US19/56163, dated Jan. 13, 2020, 11 pages.

(Continued)

*Primary Examiner* — Jason M Sims
*Assistant Examiner* — James Stewart Stambaugh, III
(74) *Attorney, Agent, or Firm* — Fenwick & West LLP

(57) ABSTRACT

A device for simultaneously acquiring electrocardiogram (ECG) signals, impedance plethysmogram (IPG) signals, ballistocardiogram (BCG) signals, and weight measurements through feet of a user. The device includes an electrically-conductive surface for contacting feet of the user and supporting weight of the user during use. The device also includes one or more force sensors for detecting forces and force variations across the electrically-conductive surface, electronics for processing electrical signals generated and/or detected from the electrically conductive surface, signals from the set of force sensors, and a base containing the electronics. The base is structurally coupled to the electrically-conductive surface by a set of conductive fasteners that transmit signals from the electrically-conductive surface to the electronics. The device can also include an integrated display for providing health insights to the user.

20 Claims, 13 Drawing Sheets

Related U.S. Application Data

(60) Provisional application No. 62/191,318, filed on Jul. 10, 2015.

(51) Int. Cl.
*A61B 5/0535* (2021.01)
*A61B 5/0205* (2006.01)

(52) U.S. Cl.
CPC ......... *A61B 5/0006* (2013.01); *A61B 5/02055* (2013.01); *A61B 5/7203* (2013.01)

(56) References Cited

U.S. PATENT DOCUMENTS

| | | | |
|---|---|---|---|
| 5,817,031 A * | 10/1998 | Masuo | A61B 5/0537 600/547 |
| 7,163,516 B1 | 1/2007 | Pagnacco et al. | |
| 7,395,104 B2 * | 7/2008 | Mouradian | A61B 5/14532 600/345 |
| 8,007,450 B2 | 8/2011 | Williams | |
| 8,535,247 B2 | 9/2013 | Williams | |
| 8,652,070 B2 | 2/2014 | Williams | |
| 8,652,071 B2 | 2/2014 | Williams | |
| 2002/0193689 A1 | 12/2002 | Bernstein et al. | |
| 2003/0220553 A1 | 11/2003 | Axelgaard et al. | |
| 2004/0251057 A1 * | 12/2004 | Suzuki | A61B 5/0537 177/25.13 |
| 2005/0039763 A1 | 2/2005 | Kraemer et al. | |
| 2005/0171451 A1 * | 8/2005 | Yeo | A61B 5/1072 600/547 |
| 2006/0115857 A1 | 6/2006 | Keen | |
| 2006/0212484 A1 | 9/2006 | Chaffin et al. | |
| 2006/0287889 A1 | 12/2006 | Brown | |
| 2007/0276262 A1 | 11/2007 | Banet et al. | |
| 2008/0045804 A1 | 2/2008 | Williams | |
| 2008/0162183 A1 | 7/2008 | Sachanandani et al. | |
| 2008/0221404 A1 | 9/2008 | Tso | |
| 2008/0243026 A1 * | 10/2008 | Tsuji | A61B 5/0537 600/547 |
| 2009/0018453 A1 | 1/2009 | Banet et al. | |
| 2010/0094147 A1 | 4/2010 | Inan et al. | |
| 2010/0152623 A1 | 6/2010 | Williams | |
| 2011/0112443 A1 | 5/2011 | Williams | |
| 2011/0264010 A1 | 10/2011 | Williams | |
| 2013/0041235 A1 * | 2/2013 | Rogers | A61B 5/1107 600/306 |
| 2013/0131484 A1 | 5/2013 | Pernu et al. | |
| 2013/0211482 A1 | 8/2013 | Pipponen | |
| 2013/0296723 A1 | 11/2013 | Cho et al. | |
| 2013/0297217 A1 | 11/2013 | Bangera et al. | |
| 2013/0310700 A1 | 11/2013 | Wiard et al. | |
| 2014/0200469 A1 | 7/2014 | Bocko et al. | |
| 2014/0308930 A1 | 10/2014 | Tran | |
| 2014/0323824 A1 | 10/2014 | Addison et al. | |
| 2015/0164351 A1 | 6/2015 | He et al. | |
| 2015/0257679 A1 | 9/2015 | Ross | |
| 2015/0260514 A1 | 9/2015 | Menelas et al. | |
| 2015/0359441 A1 | 12/2015 | Giovangrandi et al. | |
| 2015/0362360 A1 | 12/2015 | Kovacs et al. | |
| 2018/0199824 A1 | 7/2018 | Centen et al. | |

FOREIGN PATENT DOCUMENTS

| | | |
|---|---|---|
| CN | 101065752 A | 10/2007 |
| EP | 1257318 B1 | 12/2006 |
| JP | 2002-112976 A | 4/2002 |
| JP | 3866943 B2 | 1/2007 |
| WO | WO 2013/017717 A2 | 2/2013 |
| WO | WO 2014/032181 A1 | 3/2014 |
| WO | WO 2015/195983 A1 | 12/2015 |

OTHER PUBLICATIONS

PCT International Search Report, PCT Application No. PCT/CA2015/051120, dated Apr. 12, 2016, 17 pages.
Ashley, E. A. et al., "Chapter 3: Conquering the ECG," Cardiology Explained, London: Remedica, 2004, pp. 1-34.
Malmivuo, J. et al., "Section 25.3.1 Measurement of the Impedance of the Thorax," In Bioelectromagnetism—Principles and Applications of Bioelectric and Biomagnetic Fields, New York, NY, etc. Oxford University Press, Jan. 1995, pp. 544-545.
PCT International Search Report and Written Opinion, PCT Application No. PCT/US2019/056162, dated Dec. 20, 2019, 13 pages.
Khalil, S.F et al., "The Theory and Fundamentals of Bioimpedance Analysis in Clinical Status Monitoring and Diagnosis of Diseases," Sensors, vol. 14, Jun. 19, 2014, pp. 10895-10928.
United States Office Action, U.S. Appl. No. 15/743,154, dated Oct. 2, 2020, 20 pages.
Chen, Z. et al., "Noninvasive Monitoring of Blood Pressure Using Optical Ballistocardiography and Photoplethysmograph Approaches," 35th Annual International Conference of the IEEE EMBS, Jul. 2013, pp. 2425-2428.
Deb, S. et al., "Cuff-less Estimation of Blood Pressure using Pulse Transit Time and Pre-ejection Period," 2007 International Conference on Convergence Information Technology, Nov. 2007, pp. 941-944.
Díaz, D. H. et al., "Heart Rate Detection from Single-Foot Plantar Bioimpedance Measurements in a Weighing Scale," 32nd Annual International Conference of the IEEE EMBS, Aug. 2010, pp. 6489-6492.
Garrard, C. L. et al., "The Relationship of Alterations in Systolic Time Intervals to Ejection Fraction in Patients with Cardiac Disease," Circulation, 42(3), Sep. 1970, pp. 455-462.
Omron Healthcare, Inc., "Omron Instruction Manual Body Composition MONITOR with Scale Model HBF-SOOCAN," 2009, pp. 1-44, [Online] Retrieved from the Internet <URL: https://www.omronhealthcare.ca/wp-content/uploads/hbf—500can7im7eng704142010.pdf>.
Pathway Medicine, "Breathing Cycle," Mar. 24, 2015, two pages, {online] Retrieved from the Internet Archive <URL: https://web.archive.org/web/20150324095850/http://www.pathwaymedicine.org/breathing-cycle>.
United States Office Action, U.S. Appl. No. 15/743,154, filed Aug. 18, 2021, 26 pages.

* cited by examiner

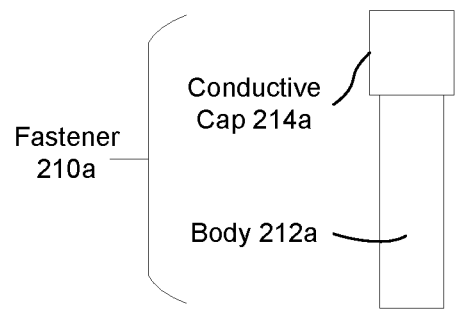
FIG. 2A
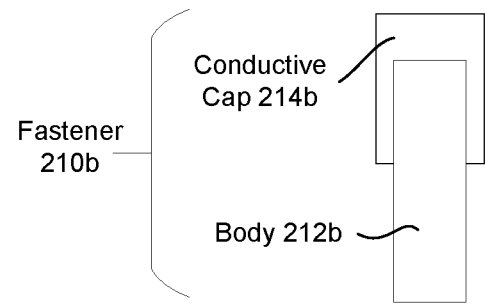
FIG. 2B
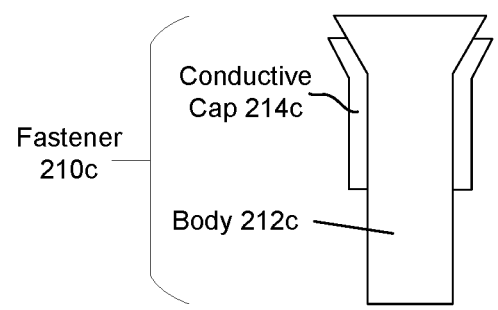
FIG. 2C
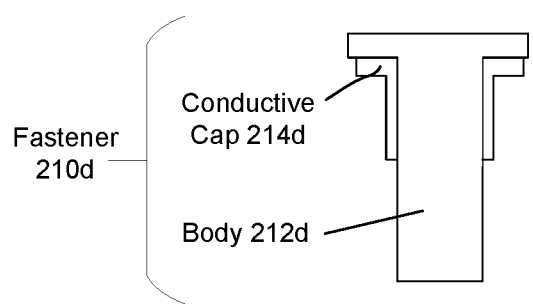
FIG. 2D
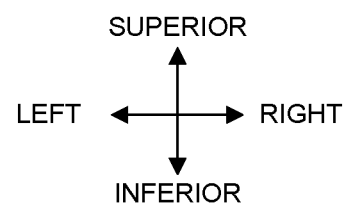

CARDIOVASCULAR HEALTH MONITORING DEVICE

CROSS REFERENCE TO RELATED APPLICATIONS

This application is a continuation-in-part of co-pending U.S. application Ser. No. 15/743,154, filed on Jan. 9, 2018, which is a National State Entry of International Application No. PCT/CA2015/051120, filed on Nov. 2, 2015, which claims the benefit of priority to U.S. Provisional Application No. 62/191,318, filed on Jul. 10, 2015, all of which are incorporated by reference herein in their entirety. This application is also related to U.S. patent application Ser. No. 16/163,343, filed on an even date herewith, and titled "CARDIOVASCULAR SIGNAL ACQUISITION, FUSION, AND NOISE MITIGATION," and is also related to U.S. patent application Ser. No. 16/163,349, filed on an even date herewith, and titled "CARDIOVASCULAR SIGNAL ACQUISITION, FUSION, AND NOISE MITIGATION," the contents of both are hereby incorporated by reference.

BACKGROUND

This disclosure relates generally to user health monitoring, and more specifically to a device for acquiring and processing biometric signals.

About 1 of 3 U.S. adults (over 70 million people) have high blood pressure, but only approximately half of these individuals have their high blood pressure under control. High blood pressure is often called a "silent killer" because it typically produces no warning signs or symptoms, but is associated with increased risk factors for more serious conditions, such as heart disease and stroke. Frequent monitoring of blood pressure and other biometric parameters can enable early detection of abnormal or deteriorating health states; however, currently available home-use devices (e.g., pneumatic cuffs) are not user-friendly, are uncomfortable, are difficult to use, and are not designed to promote regular use, in relation to adherence to a health-monitoring regimen. Even further, devices for consumer use are limited in the types of signals they can acquire and effectively process to generate composite features relevant to different health states.

SUMMARY

Disclosed is a device for simultaneously acquiring electrical and/or force signals through feet of a user, where the electrical signals can include electrocardiogram (ECG) signals and/or impedance plethysmogram (IPG) signals, and the force-derived signals can include ballistocardiogram (BCG) signals and weight measurements. The device includes an electrically-conductive surface for contacting feet of the user and a substrate for supporting weight of the user during use. The device also includes one or more force sensors for detecting forces and force variations through the electrically-conductive surface, electronics for processing electrical signals generated from the electrically conductive surface and signals from the set of force sensors, and a base containing the electronics. The base is structurally coupled to the electrically-conductive surface by a set of conductive fasteners that transmit signals from the electrically-conductive surface to the electronics. The device can also include an integrated display for providing health insights to the user in different operation modes.

BRIEF DESCRIPTION OF THE DRAWINGS

FIG. 2A is a cross sectional view of a first embodiment of a fastener of a system for health monitoring.

FIG. 2B is a cross sectional view of a second embodiment of a fastener of a system for health monitoring.

FIG. 2C is a cross sectional view of a third embodiment of a fastener of a system for health monitoring.

FIG. 2D is a cross sectional view of a fourth embodiment of a fastener of a system for health monitoring.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

1. System for Health Monitoring

Figure 1A:
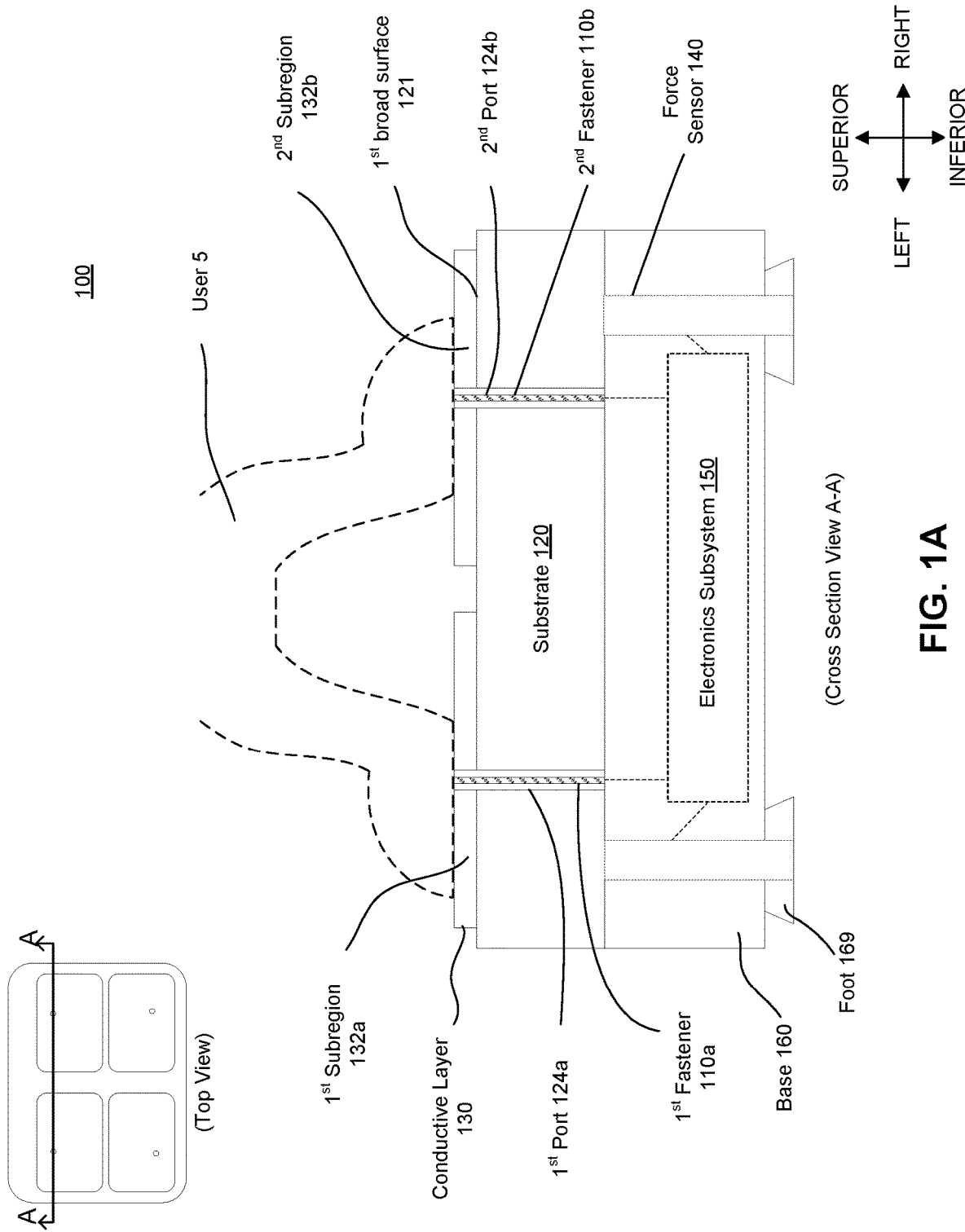
FIG. 1A is a schematic of a system for health monitoring, in accordance with one or more embodiments.
Figure 1B:
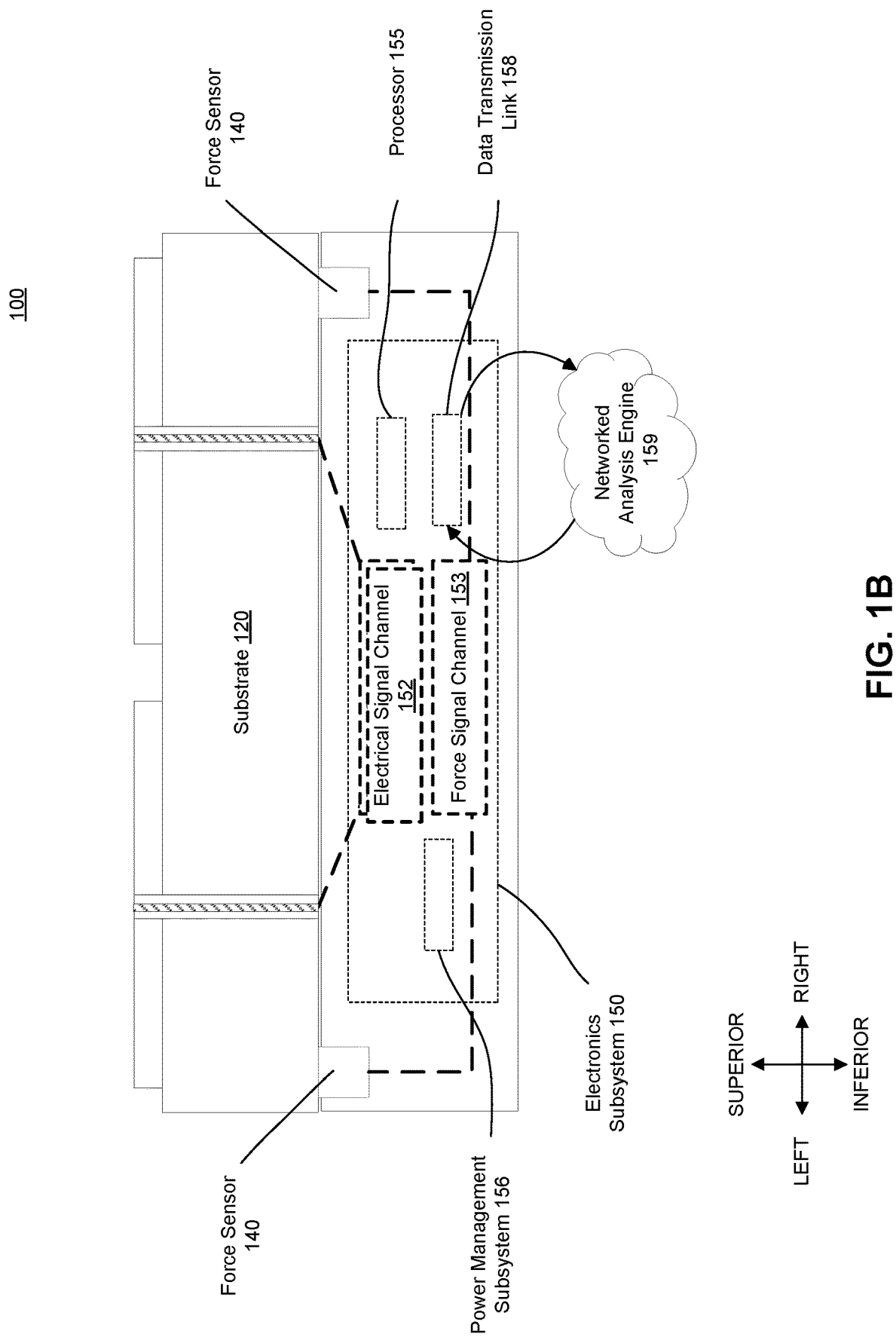
FIG. 1B is a schematic of a portion of the system shown in FIG. 1A, in accordance with one or more embodiments.

FIG. 1A is a schematic of a system 100 for health monitoring, in accordance with one or more embodiments and FIG. 1B is a schematic of a portion of the system 100 shown in FIG. 1A, in accordance with one or more embodiments. The system 100 includes a first fastener 110a and a second fastener 110b, each of the first fastener 110a and the second fastener 110b comprising a body 112 and a conductive cap (described and shown in more detail below) coupled to an end region of a body 112. The system 100 further includes a substrate 120 with a first port 124a and a second port 124b each passing into a first broad surface 121 of the substrate 120. The first port 124a retains the first fastener 110a in position and the second port 124b retains the second fastener 110b in position, to facilitate coupling between elements of the system 100. The first broad surface 121 of the substrate 120 is coupled to a conductive layer 130.

The conductive layer 130 is separated into a first subregion 132a electrically coupled to a conductive portion of the first fastener 110a and a second subregion 132b electrically coupled to a conductive portion of the second fastener 110b. The first subregion 132a is electrically isolated from the second subregion 132b to prevent electrical bridging across the first subregion 132a and the second subregion 132b. The system 100 can also include a base 160 that functions to house or otherwise support one or more elements of the system 100, as described in more detail below. The base 160 is supported by the feet 169, and the feet 169 function as the points of contact between the base 160 and the ground.

The system 100 can also include a set of force sensors 140 in communication with the substrate 120 and an electronics subsystem 150, where the set of force sensors 140 function to generate and transmit force-derived signals that can be processed simultaneously with the electrical signals to derive comprehensive insights into a user's health and/or for noise mitigation purposes. The set of force sensors 140 can thus measure static and dynamic loads transferred to the substrate 110 when a user interacts with the system 100 The set of force sensors 140 form the main point of contact between the substrate 110 or the base 160, and feet 169. In one embodiment, the system 100 includes four force sensors positioned proximal the corners of the substrate 100 each sensor configured to a foot 169; however, in alternative embodiments, the system 100 can include other suitable numbers of force sensors positioned relative to the substrate 110 in another manner. In the embodiment of FIG. 1A, the set of force sensors 140 are load cells configured to generate an electrical signal that is proportional to a force being measured.

The electronics subsystem 150 shown in FIG. 1B includes an electrical signal channel 152 electrically coupled to the first fastener 110a and the second fastener 110b and a force signal channel 153 electrically coupled to the set of force sensors 140, and can include additional electrical signal channels and/or force signal channels (not shown in the cross-section view). The electrical signal channel 152 may transmit various bio-electrical signals such as electrocardiogram (ECG) and impedance plethysmogram (IPG), and the force signal channel 153 may transmit signals such as ballistocardiogram (BCG) signals and weight signals. The electronics subsystem 150 can also include current output circuitry that injects a current (e.g., a current less than 1 mA, a current less than 5 mA, etc.) at a frequency (e.g., 2-100 kHz) in order to detect active electrical signals, such as IPG signals, from the user as the user interacts with the system 100. The electronics subsystem 150 can include a power management subsystem 156 that provides power to one or more components of the system 100, a data transmission link 158 for transmission of data to remote computing systems (e.g., such as a remote computing system hosting the network analysis engine 159 described below), and a processor 155 for providing control instructions to controllable elements of the system and/or coordinating operation states of the system 100. A networked analysis engine 159 can be in communication with the data transmission link 158 of the electronics subsystem 150. As such, the networked analysis engine 159 can be hosted remotely and can operate to process electrical data inputs and force-derived data inputs. The networked analysis engine 159 can also transmit outputs to other systems to promote health of a user interacting with the system 100.

The system 100 functions to provide a device that is user-friendly, comfortable, and configured to promote regular (e.g., daily, weekly, etc.) use by a user. The system can provide multiple types of signals that are relevant to different health states (e.g., different cardiovascular health states, other health states). The system can also provide an in-home solution that promotes regular use in order to encourage early detection of health issues, in particular cardiovascular health issues. In one or more embodiments, the system 100 can include a device having a form factor and functionality of a weighing scale, such that the device, while a user undergoes a routine weighing process, automatically generates electrical signal data and force signal data that can be co-processed for monitoring user health. As such, the device can be configured to unobtrusively and non-invasively collect and fuse multiple signal types, without overburdening the user.

1.1 System—Fasteners

In relation to FIG. 1A, the first fastener 110a and the second fastener 110b function to simultaneously provide structural support to and to couple elements of the system together (e.g., the substrate 120 to the base 160). The first fastener 110a and/or the second fastener 110b can additionally include electrically conductive regions that facilitate transmission of electrical signals generated in response to interactions with the feet of the user to the electronics subsystem 150. One or more portions of the first fastener 110a and/or the second fastener 110b can also function to seal respective openings in surfaces (e.g., a surface of the substrate 120, a surface of the base 160 of elements of the system 100, etc.) to protect sensitive components (e.g., components of the electronics subsystem 150) from fluid ingress during use of the system 100 by a user, or while stationed in an ambient environment.

The fasteners (e.g., fastener 110a, fastener 110b) can include one or more of: a screw, a pin, a nail, a bolt, or another fastener having another form factor. A portion (e.g., a first end region, a second end region) of a fastener can be threaded in order to cooperate with other retaining elements for coupling portions of the system 100 together. For instance, as shown in FIG. 1A, the first fastener 110a can pass into a first port 124a of the substrate 120 and the second fastener 110b can pass into a second port 124b of the substrate 120 to physically couple the substrate 120 to the base 160 and/or provide electrical coupling with the conductive layer 130.

As shown in FIG. 1A, the first fastener 110a and the second fastener 110b do not protrude from a surface of the conductive layer 130 configured to interface with the user, in relation to user comfort considerations. As such, a surface (e.g., head region) of a fastener can be flush with a surface of conductive layer 130, in order to enable mating of two surfaces (e.g., co-planar surfaces, concentrically-oriented surfaces, other surfaces of the fastener(s) and of the conductive layer). This configuration enhances the reliability of the interconnection between the fastener(s) and the conductive layer, in comparison to point coupling with a conductive element. The interaction between the fastener (e.g., first fastener 110a, second fastener 110b) and its surrounding components (e.g., the conductive layer 130) is described in greater detail below in relation to FIG. 7A. Alternatively, one or more portions of a head region of a fastener can be recessed within the conductive layer 130 and/or the substrate 120. In alternative embodiments, however, one or more regions of a fastener can protrude from a surface of the substrate 120 and/or conductive layer 130.

In relation to mechanical properties, the material(s) of the fastener 110a and/or the fastener 110b can have a compressive strength, a shear strength, a tensile strength, a strength in bending, an elastic modulus, a hardness, a derivative of the above mechanical properties and/or other properties that enable structural support of the user and/or other system elements in various operation modes associated with use of the system 100.

As described above, the first fastener 110a and/or the second fastener 110b can function to transmit electrical signals detected from the body of the user 105 (e.g., through the feet of the user 105), where the electrical signals can be associated with electrocardiogram (ECG) signals and/or impedance plethysmography (IPG) signals. Additionally or alternatively, the electrical signals can include one or more of: electromyography signals, body impedance/body composition, galvanic skin response or skin conductance signals, or other bioelectrical signals. As such, in relation to electrical properties, the material(s) of the first fastener 110a and the second fastener 110b can have a conductivity, resistivity, a derivative of the above electrical properties and/or other properties that enable electrical signal transmission from the conductive layer 130 to the electronics subsystem 150. The material(s) of a first fastener 110a and a second fastener 110b can alternatively be selected to have desired electrical properties.

The fasteners (e.g., first fastener 110a, second fastener 110b) can thus be composed of a conductive material such as a metal, a conductive polymer, or another conductive material, in order to facilitate signal transmission. As described below, one or more embodiments of the fasteners (e.g., first fastener 110a, second fastener 110b) can be configured as a composite of multiple materials corresponding to different regions of a respective fastener, where the different regions and materials provide different functionalities. In relation to measurement of electrical signals, the conductive material(s) of the fasteners (e.g., first fastener 110a, second fastener 110b) can have a maximum resistivity of 5 Ohms. Alternatively, the material of the fasteners can have any suitable resistivity.

Several embodiments of a fastener (e.g., fastener 210a, 210b, 210c, 210d) are illustrated by the cross sectional views of FIG. 2A-2D. As shown in FIGS. 2A-2D, embodiments of a fastener can include a body (e.g., body 212a, 212b, 212c, 212d) and a conductive cap (e.g., conductive cap 214a, 214b, 214c, 214d). The body can be composed of a conductive material such as stainless steel, copper, and/or aluminum. The conductive cap can be composed of a conductive polymer such as a rubber (e.g. carbon doped silicone) or a conductive plastic. Alternatively, the conductive cap can be composed of another material such as a soft metal. In particular, the conductive cap is made of a material that is softer than material of the substrate in order to provide electrical coupling to the conductive layer (e.g., through multiple points or a region of contact) and compliance to protect the substrate from the fastener (e.g., to provide shock absorption). As described in more detail below, the conductive cap can be configured in a manner that can expose one or more portions of the fastener. For instance, the conductive cap can expose a top portion of a core material of the fastener, can ensheathe a bottom of a head region of the fastener, or surround a bottom region and/or body of the fastener. Alternatively, the different regions of the fasteners (e.g., 210a, 210b, 210c, 210d) can be composed of any suitable material.

The longitudinal cross section of the body (212a, 212b, 212c, and 212d) of a fastener shown in FIGS. 2A-2D is circular. However, in alternative embodiments, the longitudinal cross section of the body can be ellipsoidal, polygonal, or any other suitable shape. The conductive cap (e.g., conductive cap 214a, 214b, 214c, 214d) can be flat or convex or concave along an axial direction of a fastener. Furthermore, the cross section of the body (e.g., body 212a, 212b, 212c, and 212d) and the conductive cap (e.g., conductive cap 214a, 214b, 214c, 214d) can be constant or variable along the length of the body.

As shown in FIG. 2A, a first embodiment of a fastener 210a includes a body 212a and a conductive cap 214a. FIG. 2A is a first embodiment where the conductive cap 214a is coupled to an end region of the body 212a (e.g., an end region configured to interface with a conductive layer) of the fastener 210a. In the first embodiment, the width of the conductive cap 214a is greater than the width of the body 212a.

FIG. 2B is a second embodiment of a fastener 210b including a conductive cap 214b ensheathing a body 212b of a fastener 210b. In the second embodiment, the conductive cap 214b is coupled to an end region and extends at least partially down the longitudinal side of the body 212b of the fastener 210b. The width of the conductive cap 214b is greater than the width of the body 212b.

FIG. 2C is a third embodiment of a fastener 210c with a conductive cap 214c and a body 212c. The conductive cap 214c is coupled to the sides of the body 212c of the fastener 210c, under a head region of the fastener 210c. In the embodiment of FIG. 2C, the conductive cap 214c does not interface with the superior surface of the body 212c, such that the superior surface of the body 212c is uncovered by the conductive cap 214c and exposed. The conductive cap 214c functions as a conical sheathing to couple the body 212c to surrounding components, as described below in relation to FIG. 7A.

FIG. 2D is a fourth embodiment of a fastener 210d including a conductive cap 214d and a body 212d. The conductive cap 214d is coupled to the sides of the body 212d of the fastener 210d, under a head region of fastener 210d. The body 212d is T-shaped (in a longitudinal cross section) and the conductive cap 214d is configured as a sheath below the flange of the body 212d to couple the body 212c to the surrounding components, as described below in relation to FIG. 7A. Additionally, the superior surface of the body 212d is uncovered by the conductive cap 214d and exposed.

FIGS. 2C and 2D thus depict fastener configurations that have mating contacting faces over a wide surface area, where coupling of an interface (e.g., self-centering countersunk interface of the substrate) with a compliant interface material between the conductive layer coupled to the substrate (described in more detail below) and a respective fastener body provide desired mechanical and electrical contact characteristics.

Figure 3:
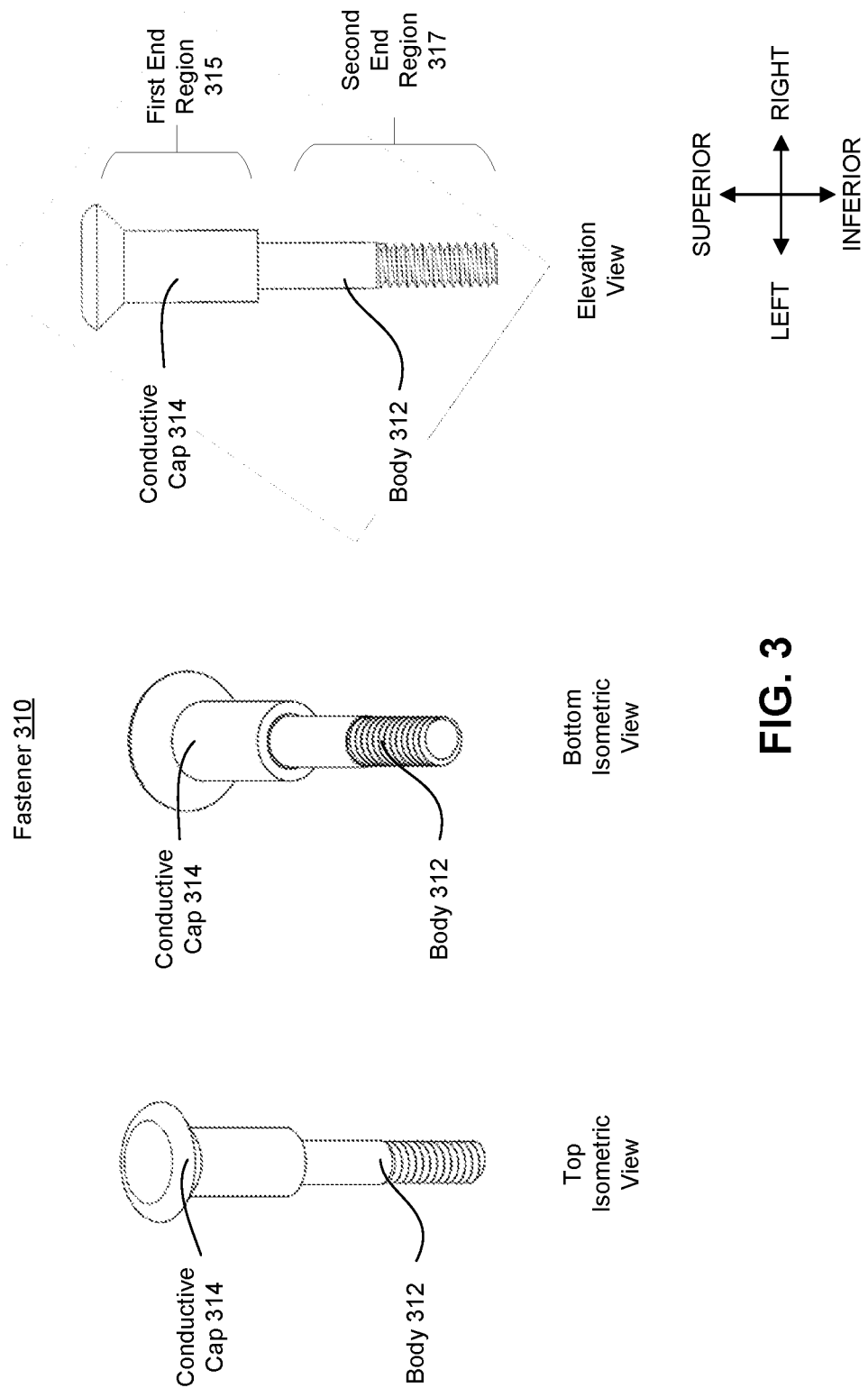
FIG. 3 depicts a top isometric view (left), a bottom isometric view (middle), and an elevation view (right) of an embodiment of a fastener of a system for health monitoring.

As described above in relation to FIGS. 1A-1B and 2A-2D, a fastener can have characteristics (e.g., morphological characteristics, region-specific characteristics, electrical properties, mechanical properties, etc.) that vary depending upon the embodiment and requirements of the system 100. One such embodiment is shown in FIG. 3, where FIG. 3 includes a top isometric view (left), a bottom isometric view (middle), and an elevation view (right) of an embodiment of a fastener 310 of a system 100 for health monitoring. The fastener 310 shown in FIG. 3 includes a body 312 composed of stainless steel and a conductive cap 314 composed of carbon-doped rubber; however, the fastener 310 and conductive cap 314 can alternatively be composed of other suitable materials, as described above. The fastener 310 shown in FIG. 3 has a length of 20.8 millimeters and 6 millimeters of M2.5 thread on the second end region 317 of the fastener 310. The second end region 317 has a diameter of 2.3 millimeters and the first end region 315 has a diameter of 2.5 millimeters. In alternative embodiments, however, the fastener can have a length of 5-80 millimeters and a first end region 315 and/or a second end region 317 diameter of 0.5-15 millimeters. The fastener 310 includes a conductive cap 314 with a thickness of 0.55 millimeters ensheathing the first end region 315 of the fastener 310. In alternative embodiments, however, the conductive cap 314 can have a thickness of 0.1-10 millimeters. The fastener 110 including the conductive cap 314 can alternatively have any other suitable dimensions.

The fastener 310 described by FIG. 3 can have characteristics that vary depending upon the embodiment and the requirements of the system 100. For example, the fastener can have a conductive cap ensheathing both the first end region 315 and the second end region 317 functioning to seal at least a portion of the system, as described above. Furthermore, the fastener 310 can omit some elements shown by FIG. 3. For example, the fastener 310 can have a conductive body 312 without a conductive cap 314 to simplify the system 100 for various purposes (e.g., simplify the manufacturing process, promote easy repair, etc.).

1.2 System—Substrate

As shown in FIGS. 1A and 1B, the system includes a substrate 120 that functions as a surface on which to bond the conductive layer 130. The substrate 120 facilitates electrical signal transmission from the conductive layer 130 (described below), through the fasteners, and toward the electronics subsystem 150. The substrate 120 can also function to mechanically support the weight of a user 105 in relation to weight measurements and other force-associated signal generation functionality. The substrate 120 can additionally function to enable display (e.g., with integrated display elements, with transparent materials, with translucent materials, etc.) of information to the user 105 described in later sections. The information can include information derived from analyses of signals generated by the system, instructions to the user, user verification information, or other types of information.

In morphology, the substrate 120 includes a first broad surface 121 to which the conductive layer 130 is coupled. The substrate 120 can also include a second broad surface to which one or more other elements of the system 100 are coupled, such as the base 160 described in more detail below. The first broad surface 121 of the substrate 120 is planar, but can alternatively include recessed and/or protruding regions defined at the broad surface. Recessed and/or protruding regions of the first broad surface 121 can be configured to guide placement of the feet of the user and can include features that are complimentary to the soles of the user's feet.

In relation to material composition, the substrate 120 can be composed of a single material or a composite material to provide suitable physical properties for support of the system 100 and the user 105. For example, the substrate 120 can be composed of glass (e.g., tempered glass, frosted glass, float glass, chemically strengthened glass). Alternatively, the substrate can be composed of a metal, ceramic, natural stone, polymer, composite, or any combination of materials.

In relation to mechanical properties, the material(s) of the substrate 120 can have a compressive strength, a shear strength, a tensile strength, a strength in bending, an elastic modulus, a hardness, a derivative of the above mechanical properties and/or other properties that provide adequate structural support in unloaded states and/or loaded states (e.g., with the user 105 standing on the substrate) in relation to various operation modes associated with use of the system 100.

In relation to electrical properties, the material(s) of the substrate 120 can have a conductivity, resistivity, a derivative of the above electrical properties and/or other properties that support electrical signal transmission from the user's body to the electronics subsystem 150. The substrate 120 can be composed of an insulative material to function to prevent bridging between selectively conductive regions (e.g., of the conductive layer 130 described in more detail below), and/or to prevent excess noise propagating through the system from the conductive layer 130. The bulk material(s) of the substrate 120 can alternatively be selected to have desired electrical properties.

In relation to optical properties, the material(s) of the substrate 120 can have a transparency or translucency suitable of conveying information to the user by way of an electronic display coupled to, positioned next to, or otherwise optically integrated with the substrate 120 in another manner. In other embodiments, the substrate 120 can be an opaque material. The material(s) of the substrate 120 can also be fabricated to or otherwise include optical elements (e.g., lenses, mirrors, filters, waveguides, etc.) manipulate (e.g., reflect, scatter, guide, shape, etc.) light.

Figure 4:
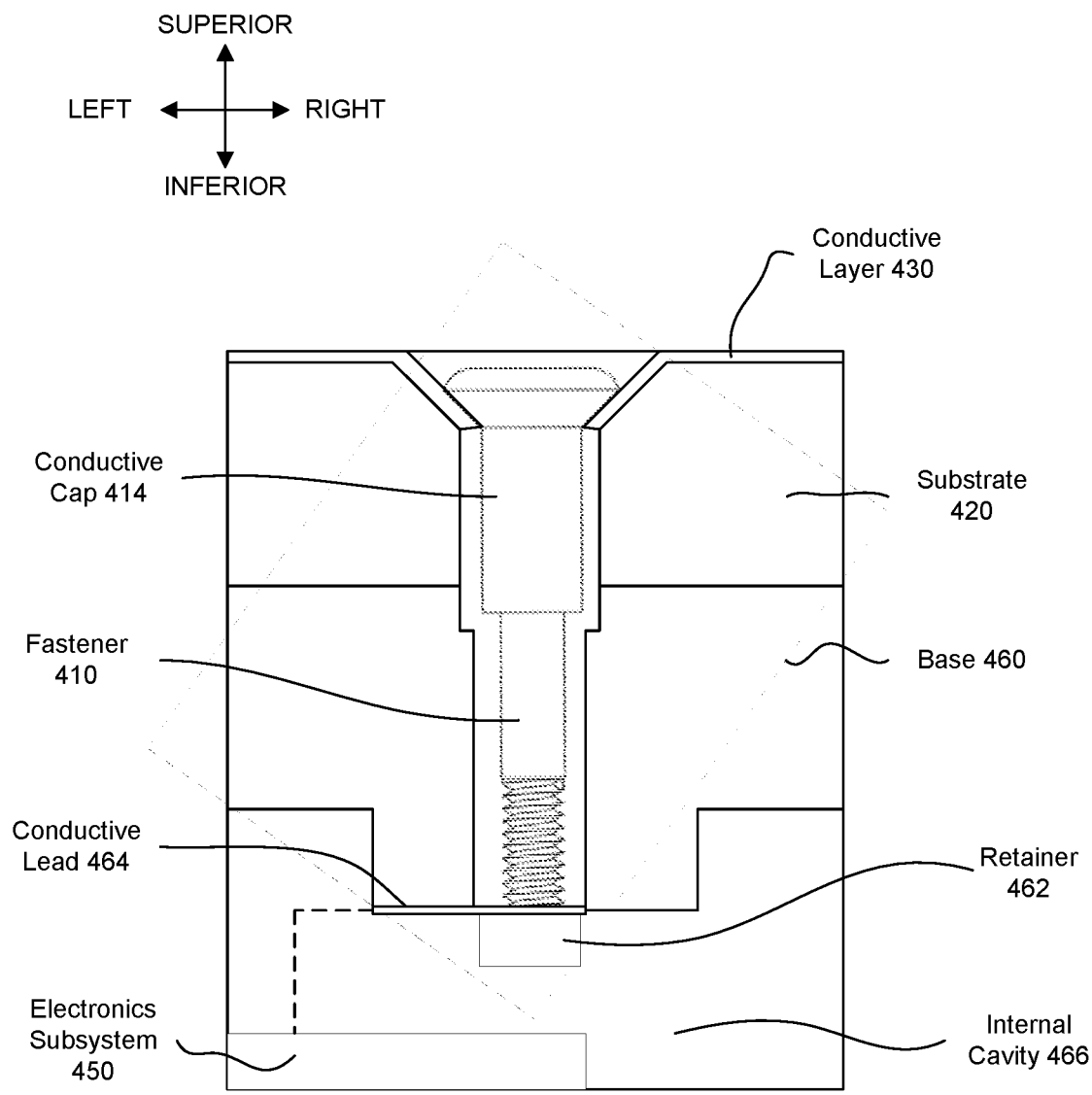
FIG. 4 is a schematic of a portion of an embodiment of a system for health monitoring.

Shown in FIG. 4, a schematic of a portion of an embodiment of a system 100 for health monitoring includes a substrate 420 coupled to a base 460 at one or more positions of its broad surfaces. In one embodiment, the substrate 420 is coupled to a conductive layer 430 and a base 460 by one or more fasteners, including fastener 410 shown in the partial cross section view of FIG. 4. The fastener 410 shown in FIG. 4 is electrically coupled to the conductive layer 430 by a conductive cap 414. A second end region of the fastener 410, away from the conductive cap 414, is electrically coupled to a conductive lead 464 and is retained in position by a retainer 462 where, in variations, the retainer 462 can secure the fastener to a base, thereby coupling the substrate 420 to a base. The conductive lead 464 is electrically coupled to an electronics subsystem 450 which is housed in an internal cavity 466 of the device. According to the embodiment of FIG. 4, the substrate 420 functions to serve as a foundation or support for other system 100 components.

1.3 System—Conductive Layer

As shown in FIG. 1A, a conductive layer 130 is coupled to the substrate 120 and includes a set of subregions in electrical communication with the first fastener 110a and the second fastener 110b. The conductive layer 130 provides an interface to the feet of the user 105 for electrical signal acquisition. The conductive layer 130 has at least one broad surface that is planar (e.g., as a thin film coupled to or patterned onto the substrate 120). Alternatively, the conductive layer can include recessed and/or protruding regions defined at the broad surface. Recessed and/or protruding regions of the broad surface can be configured to guide placement of the feet of the user and can include features that are complimentary to the soles of the user's feet. The conductive layer can thus vary in shape and size. According to the embodiment shown by FIG. 1A, the conductive layer 130 includes at least two electrically isolated subregions 132a and 132b, containing a first port 124a and a second port 124*b*, respectively, to enable distinct signal routing from individual feet of the user, through respective subregions, and through respective fasteners, as described above. Various configurations of the conductive layer 130 are demonstrated by FIG. 5 described in greater detail below.

In material composition, the conductive layer 130 is composed of a conductive material that is safe for user interaction. The conductive layer 130 can be composed of waterproof or water resistant material (e.g., such that the user 105 can interact with the system directly after showering and/or the system can operate correctly within an environment with moisture). The conductive layer 130 can be composed of a material that is resistant to rust and not easily corrodible as the system may be stored in a bathroom where it is exposed to steam from a shower or bath. The conductive layer 130 can thus be composed of a single material or can be a composite material that provides suitable physical properties.

In relation to mechanical properties, the material(s) of the conductive layer 130 can have a compressive strength, a shear strength, a tensile strength, a strength in bending, an elastic modulus, a hardness, a derivative of the above mechanical properties and/or other properties that enable structural support of the user and/or other system elements in various operation modes associated with use of the system 100. The material of the conductive layer 130 can have a hardness above a certain threshold such that minor scratches do not affect the aesthetic integrity or functionality of the system 100.

In relation to electrical properties, the material(s) of the conductive layer 130 can have a conductivity, resistivity, a derivative of the above electrical properties and/or other properties that enable electrical signal transmission from the user 105 to the electronics subsystem 150. The conductive layer 130 can be composed of a material (e.g., indium tin oxide, graphene, carbon nanotubes) with a desired pattern in relation to signal transduction through the system and/or the body of the user 105. The bulk material(s) of the conductive layer 130 can alternatively be selected to have desired electrical properties.

In relation to optical properties, the material(s) of the conductive layer 130 can have a transparency or translucency suitable of conveying information to the user by way of an electronic display coupled to, positioned next to, or otherwise optically integrated with the conductive layer 130 in another manner. The material(s) of the conductive layer 130 can also be fabricated to include optical elements (e.g., lenses, mirrors, filters, waveguides, etc.) to manipulate (e.g., reflect, scatter, guide, shape, etc.) light.

Figure 5:
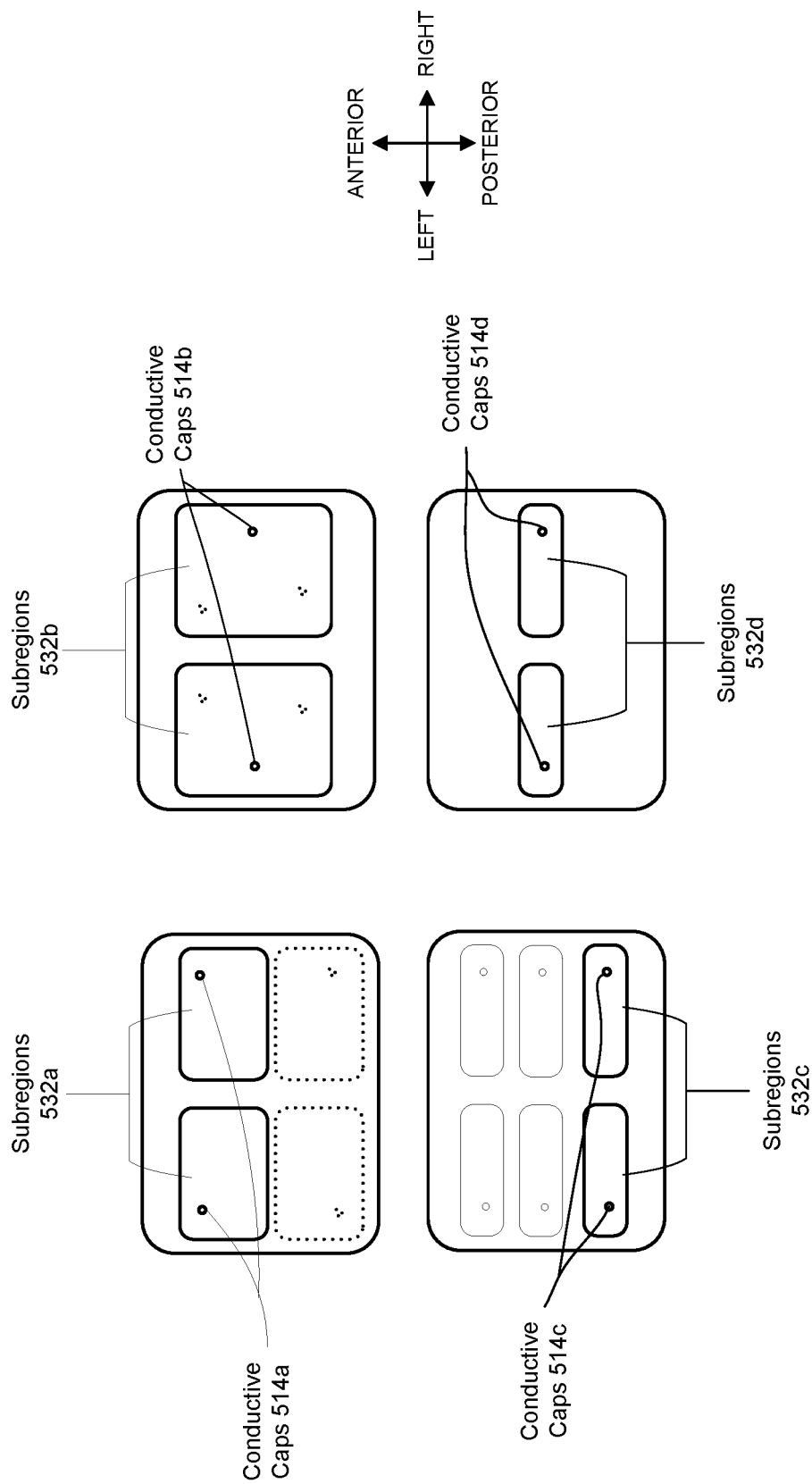
FIG. 5 depicts top views of conductive layer and conductive cap configurations of a first embodiment (top left), a second embodiment (top right), a third embodiment (bottom left), and a fourth embodiment (bottom right) of a system for health monitoring.

The subregions 132*a* and 132*b* of the conductive layer 130 can be defined at the substrate in several configurations, some variations of which are shown in FIG. 5. For instance, as shown in a first embodiment of FIG. 5 (top left), the conductive layer can be divided into a left subregion 532*a* associated with a left conductive cap of a set of conductive caps 514*a* and a right subregion 532*a* associated with a right conductive cap of a set of conductive caps 514*a*, where the left subregion is electrically separated from the right subregion (e.g., by a region that is not conductive or otherwise insulating). The first embodiment (top left) includes two optional subregions, a left posterior subregion and a right posterior subregion. The optional subregions can operate in conjunction with or in replacement of the left anterior subregion and/or the right anterior subregion. For example, electrical signals can be collected from the left posterior subregion and the right anterior subregion simultaneously. Alternatively, electrical signals can be collected from pairs of left and right subregions 532*a* such as the left and right anterior subregions or the left and right posterior subregions simultaneously.

A second embodiment (top right) of FIG. 5 illustrates a conductive layer with a left subregion associated with a left conductive cap of a set of conductive caps 514*b* and a right subregion associated with a right conductive cap of a set of conductive caps 514*b*, where the left subregion is electrically separated from the right subregion (e.g., by a region that is not conductive). The subregions 532*b* span the entire width of the system. Furthermore, each subregion 532*b* can include more than one conductive cap in each region. The optional conductive caps of the left and right subregions 532*b* can be located in any position within the subregions 532*b* and can operate in addition to or instead of the conductive caps 514*b* (e.g., if one cap fails or is otherwise compromised).

A third embodiment (bottom left) of FIG. 5 illustrates a conductive layer with three left subregions 532*c* each associated with a conductive cap of a set of conductive caps 514*c* and three right subregions 532*c* each associated with a conductive cap of a set of conductive caps 514*c*, where all of the subregions are electrically isolated (e.g., by a region that is not conductive). The subregions 532*c* can be used simultaneously for generating electrical signals from each pair of left and right foot portions or for targeting signal generation of specific portions (e.g., anterior, middle, and posterior portions) of each foot.

A fourth embodiment (bottom right) of FIG. 5 illustrates a conductive layer with a left subregion 532*d* associated with a left conductive cap of a set of conductive caps 514*d* and a right subregion 532*d* each with a conductive cap of a set of conductive caps 514*d*. The subregions 532*d* only span a portion of the width of the system and can be used for extracting electrical signals from a specific targeted region of the user feet (e.g., central region).

FIG. 5 illustrates four embodiments of the system, but is not exclusive or representative of every embodiment of the system. For example, the system can include a larger number of subregions than the amount shown by FIG. 5 for generating signals from multiple regions of each foot. The subregions can also be oriented differently, such as rotating the subregions 90 degrees or adjusting the shape and size of the subregions to satisfy design criteria (e.g., ease of manufacturing, ease of use, etc.).

Figure 6:
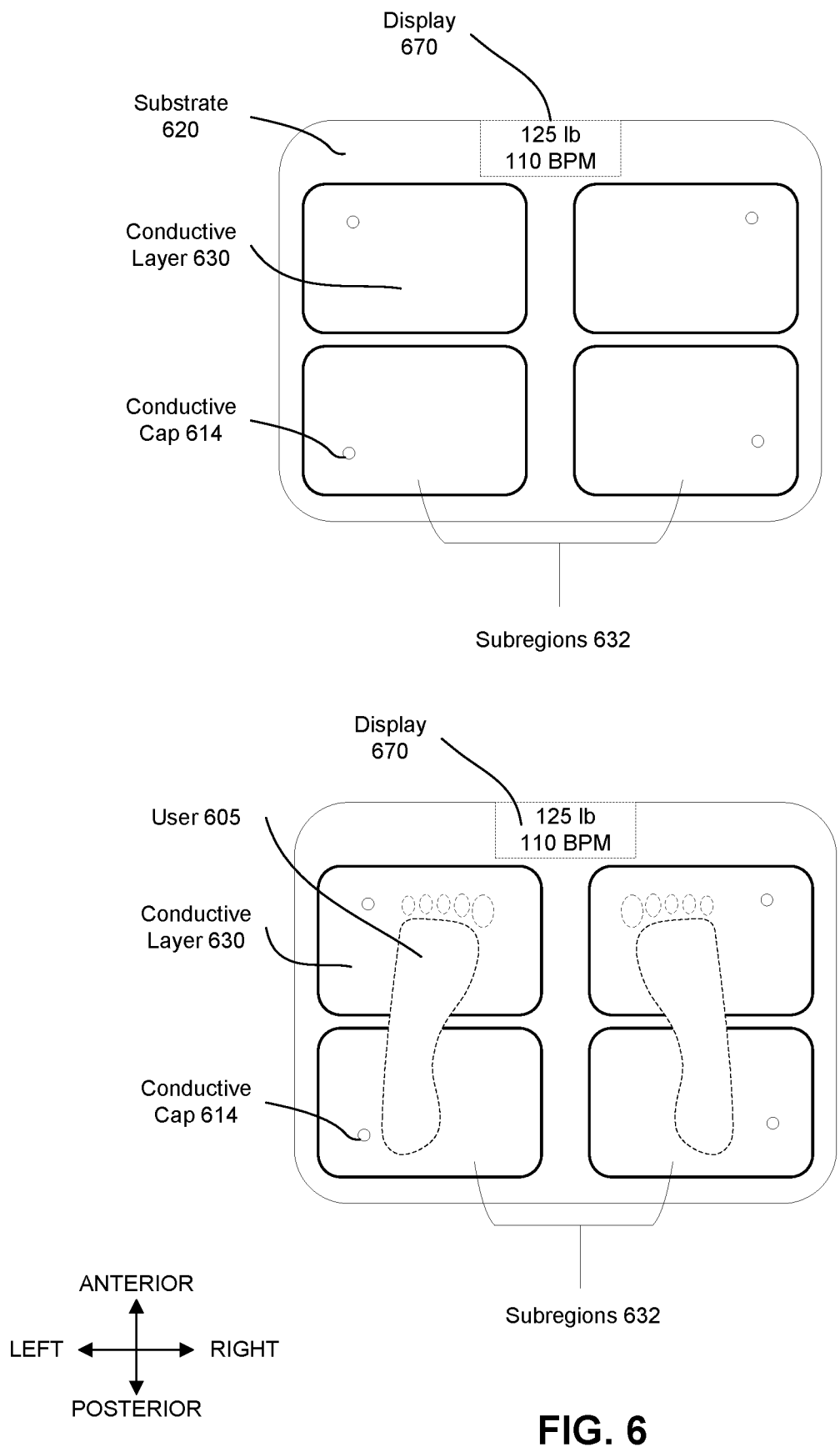
FIG. 6 is a top view of an embodiment of a system for health monitoring.

FIG. 6 is a schematic of a top view of a specific embodiment of a system for health monitoring. The embodiment in FIG. 6 illustrates a conductive layer 630 with four electrically isolated subregions 632 each with one conductive cap 614. Each subregion 632 of the conductive layer 630 has a rectangular footprint when the broad surface is projected onto a horizontal plane, where the rectangular footprint has rounded edges. The subregions 632 of the conductive layer 630 can alternatively have any other suitable footprint. For example, the subregions 632 can be one or more of: a circle, a square, or a triangle when the broad surface is projected onto a horizontal plane. In dimensions, the conductive layer 630 can have a width from 1-50 centimeters, a length from 1-50 centimeters, and a thickness from 10 nanometers to 2 centimeters; however, the conductive layer 630 can alternatively have any other suitable dimensions.

The embodiment in FIG. 6 includes a display 670 embedded in the substrate 620. The display 670 can also be embedded within the base, as described in more detail below. Alternatively, the display 670 can be contained within, coupled to, or protrude from a different or additional component of the system. For instance, a portion of the display 670 can be coupled to the substrate 620 and/or a portion can be coupled to the conductive layer 630. The display 670 can also protrude from the surface of the conductive layer 630 and/or the substrate 620.

The user 605 can interact with different subregions of the conductive layer 630 by standing on the device and having a left foot contact one or more subregions and having a right foot contact one or more subregions. As such, the user 605 can place a portion of his/her foot each subregion 632. In the embodiment of FIG. 6, the user 605 can place the anterior portion of his/her left foot in the top left subregion 632 and the anterior portion of his/her right foot in the top right subregion 632. The user 605 can place the posterior portion (e.g., heel portion) of his/her left foot in the bottom left subregion 632 and the posterior portion (e.g., heel portion of his/her right foot in the bottom right subregion 632. Alternatively, the user 605 can place his/her feet in a different direction (e.g., 90 degrees from the orientation described above, 180 degrees from the orientation described above, at another rotational angle from the orientation described above), and the system can be configured to correctly extract electrical and/or force signals (with electrical subsystem re-mapping in firmware or through another means). As such, in more detail, each subregion 632 can generate an electrical signal from the corresponding portion of the user foot. The system can be configured to detect placement of a left foot at a respective subregion 632 (e.g., based upon pressure distributions detected by the force sensors, based upon contact through capacitive sensing, based upon light transmission patterns through the substrate, etc.) and a right foot at a respective subregion 632 and to properly generate or determine an electrical signal based upon the placements of the left and the right foot. The device can measure biological signals from the user 605 as described.

1.4 System—Electronics

As shown in FIGS. 1A and 1B, the electronics subsystem 150 includes at least one electrical signal channel 152 and at least one force signal channel 153. The force signal channel 153 receives a signal from a set of force sensors 140 in order to transmit information about a user 105, in response to forces generated within or by the user's body when the user interfaces with the system 100. The force signal channel 153 can relay metrics such as body weight, ballistocardiograph (BCG) waveforms, and balance analysis. The electrical signal channel receives an electrical signal transmitted from the user 105 by a fastener 110. The electrical signal channel 152 can transmit both cardiac and non-cardiovascular metrics including pulse rate, heart rate variability (HRV), body impedance, and cardiac waveforms such as impedance plethysmograph (IPG) waveforms and electrocardiograph (ECG) waveforms. The cardiac waveforms can be analyzed by the networked analysis engine 159 or another system not shown (e.g., firmware) to evaluate cardiovascular health parameters. In specific examples, cardiovascular health parameters can include systolic time intervals such as pre-ejection period (PEP), left ventricular ejection time (LVET), pulse transit time (PTT), and pulse arrival time (PAT). The electronics subsystem 150 may also evaluate the environmental context of the device described in greater detail below.

In material characteristics, the electronics subsystem 150 can have a format that includes different materials and/or properties. For instance, the electronics subsystem 150 can include a printed circuit board (PCB), where the PCB include materials with different characteristics (e.g. flexible, rigid, ductile, brittle, etc.). The PCB can be single sided, double sided, or multi-layer. The material of the PCB can include a conductive component such as copper and a substrate composed of a dielectric composite material. Alternatively, the electronics subsystem can be composed of other suitable materials.

In relation to characteristics of the electronics subsystem 150, the electronics subsystem 150 can include circuitry characteristics configured to improve function in relation to processing of multiple types of signals, noise mitigation due to different electrical and/or mechanical factors, signal transmission, and/or other factors. For instance, the electronics subsystem 150 can include configurations where analog and/or digital components associated with different types of signals are separated from each other in relation to prevention of interference. Additionally or alternatively, the electronics subsystem 150 can include elements that promote isolation or mitigation of electrical noise sources. Additionally or alternatively, the electronics subsystem 150 can include elements that promote isolation or mitigation of mechanical or vibrational noise sources (e.g., with mechanical noise isolation elements coupled to the sensor(s), with vibration dampeners coupled to the substrate, with vibration dampeners coupled to the base, etc.). Additionally or alternatively, the electronics subsystem 150 can include architecture that promotes efficient signal transmission characteristics (e.g., can include architecture with a specified density of interconnects or distance between electronics components).

In relation to mechanical properties, the material(s) of the electronics subsystem 150 can have a compressive strength, a shear strength, a tensile strength, a strength in bending, an elastic modulus, a hardness, a derivative of the above mechanical properties and/or other properties that enable structural support of the user and/or other system elements in various operation modes associated with use of the system 100. The materials chosen can satisfy a variety of characteristics that are relevant to electronics.

In relation to electrical properties, the material(s) of the electronics subsystem 150 can have a conductivity, resistivity, a derivative of the above electrical properties and/or other properties that the electronics subsystem 150 to receive electrical signal transmission. In an embodiment, as shown in FIG. 4, an electronics subsystem 450 is electrically coupled to a conductive lead 464 in order to receive electrical signals from a fastener 410. The fastener receives and transmits an electrical signal from a conductive cap 414 to the conductive lead 464. The conductive lead can also have a conductivity, resistivity, a derivative of the above electrical properties to transmit an electrical signal from the fastener 410 to the electronics subsystem 450.

Figure 7A:
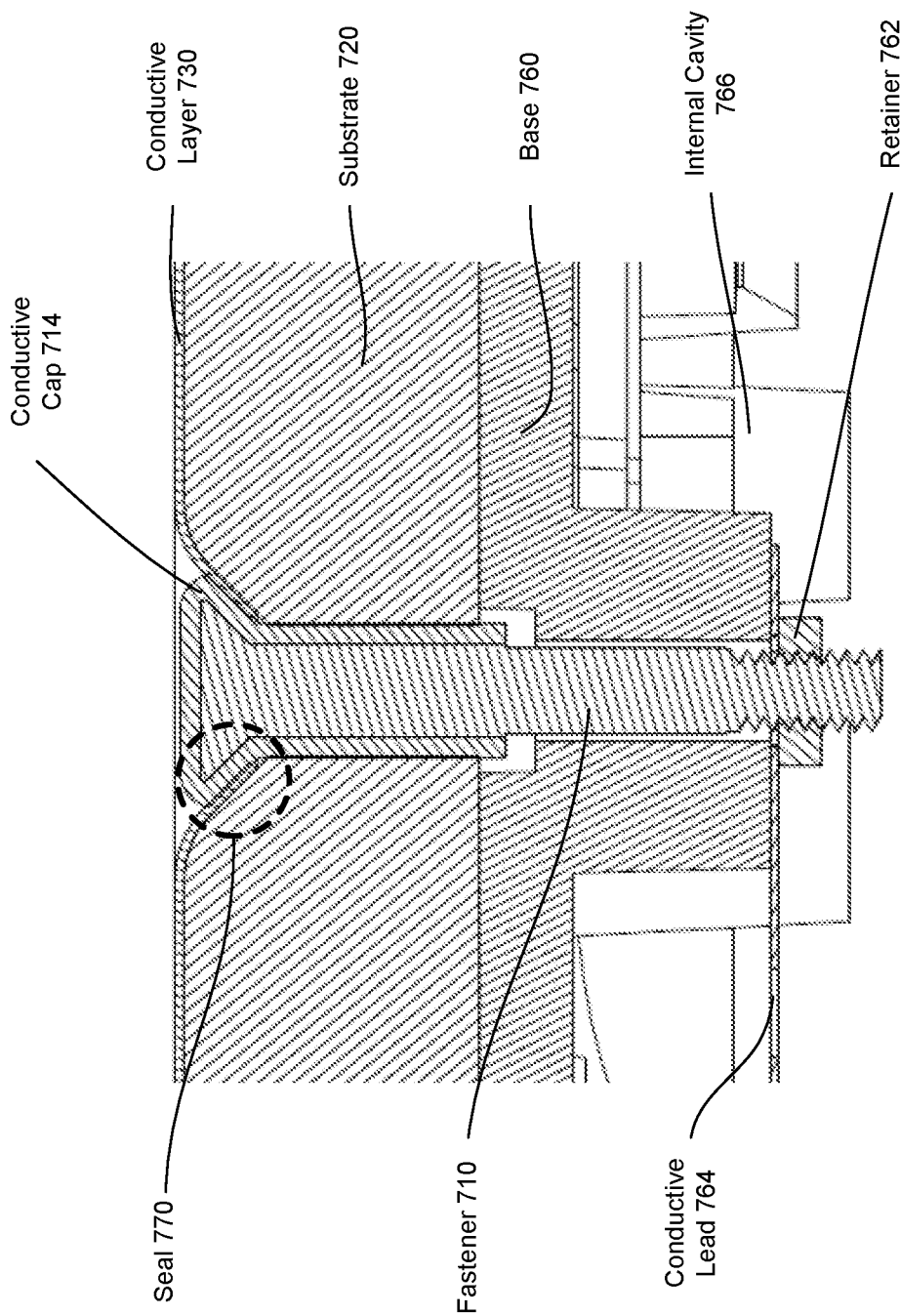
FIG. 7A is a schematic of a portion of an embodiment of a system for health monitoring.

In the configurations shown, the electronics subsystem 150 is positioned inferior to the conductive surface 120 to protect the electronics subsystem 150 from user 105 interference or other factors. In the embodiment shown in FIG. 4, an electronics subsystem 450 is contained within an internal cavity 466. In some embodiments, the internal cavity 466 can be an internal cavity of one or more of: a base 460 or the substrate 460. The base 460 can be composed of an insulative material to function to prevent excess noise propagating through the system from the conductive layer 130. The base 460 can also serve to prevent undesired signal interaction between the fastener 410 and other system components (e.g., a power subsystem, the substrate 420). Alternatively, the electronics subsystem can be coupled to the conductive layer 460 or an exterior surface of the system in another manner. In order to protect the integrity of the electrical subsystem 450, the subsystem 450 can be sealed from external dangers such as water, dirt, or other environmental conditions that may cause damage to the electrical subsystem 450. For instance, as shown in FIG. 7A (which is described in more detail below), a conductive layer 730 is coupled to a conductive cap 714 and the conductive cap comprises a compliant and conductive polymer material that cooperates with the substrate 720 to form a seal 770. The seal 770 prevents water and other fluids or particles from flowing towards an electronics system housed below the conductive layer 130.

The seal 770 formed by the conductive cap 714 composed of a compliant material also functions to interface components of the system. The conductive cap 714 provides contouring between the conductive layer 730, the substrate 720, and the fastener 710. As the fastener 710 is tightened, the conductive cap 714 fills the gaps between the fastener 710, the conductive layer 730, and the substrate 720 in order to maximize the conductive contact surface area. The conductive cap 714 also provides a mechanical connection to attach the base 760 to the substrate 720. As such, the conductive cap 714 functions as a shock absorber between the substrate 720 and the fastener 710, preventing damage to the substrate 720 or the conductive layer 730.

Figure 7B:
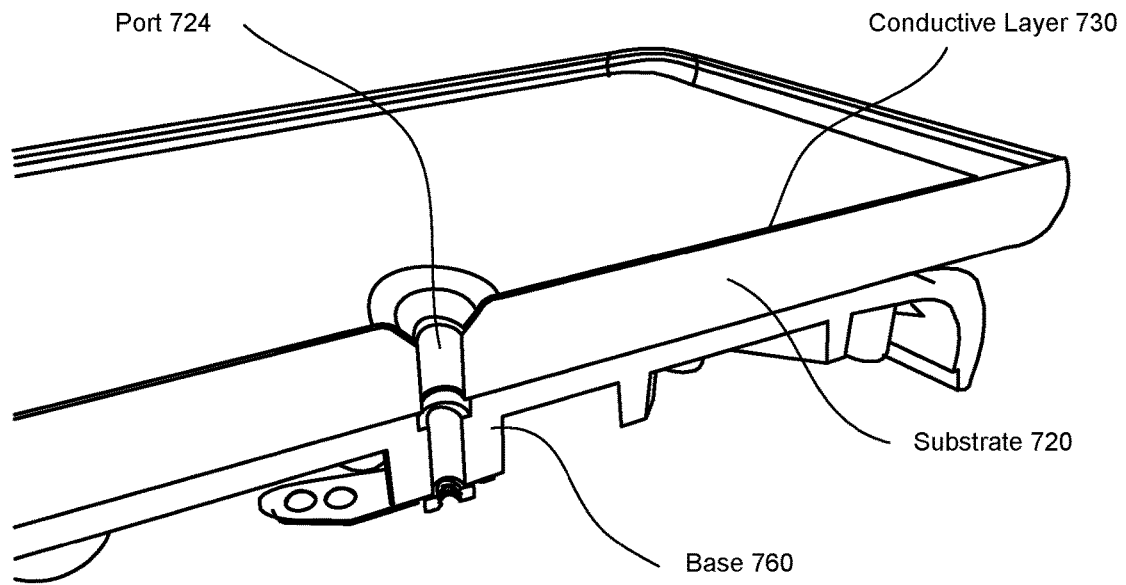
FIG. 7B is a cross section isometric view of an environment of the embodiment of the system shown in FIG. 7A.
Figure 7C:
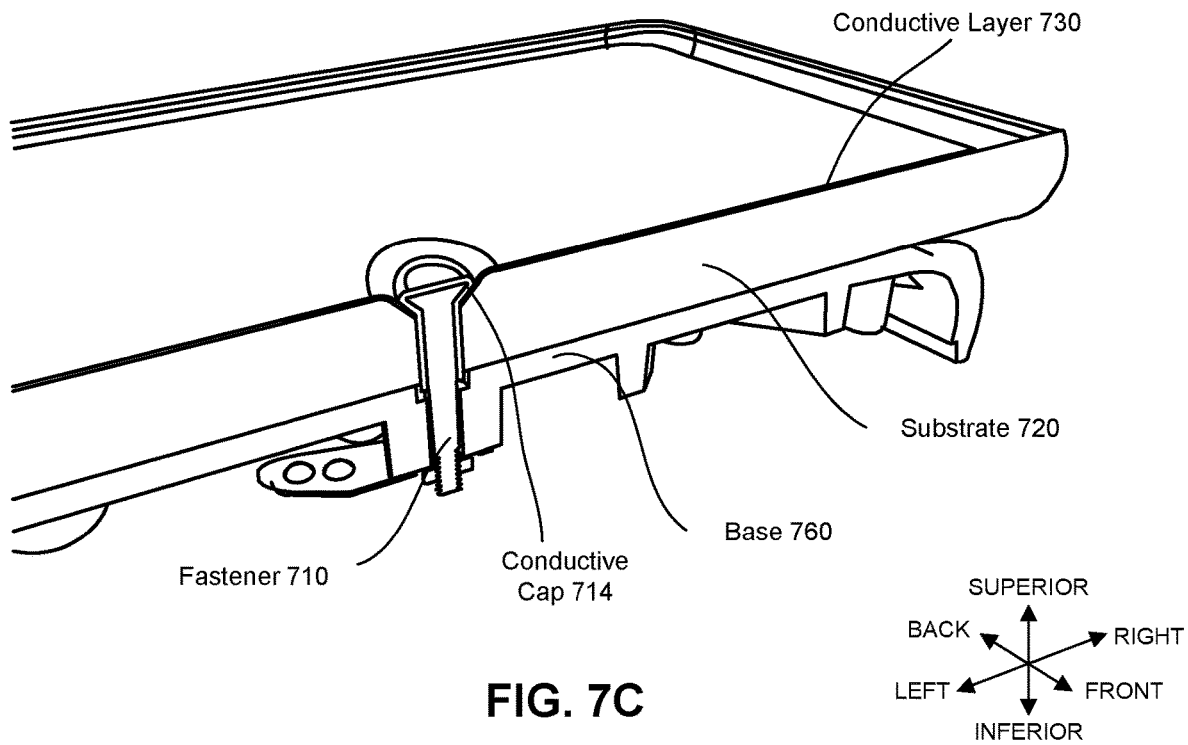
FIG. 7C is a cross section isometric view of an environment of the embodiment of the system shown in FIG. 7A.

As described above in relation to FIGS. 2C and 2D, the system configuration shown in FIGS. 7A-7C includes mating contacting faces that provide mechanical and electrical contact functionality, where coupling of an interface (e.g., self-centering counter-sunk interface of the substrate 720) with a compliant interface material of the conductive cap 714 between the conductive layer 730 coupled to the substrate 720 and a respective body of a fastener 710 provides a reliable connection (in terms of electrical contact) and allows for some shock absorption.

1.4.1 System—Additional Sensors

The system can also include or otherwise receive signals from additional sensors (e.g., temperature sensors, light sensors, moisture sensors), where additional sensors can be coupled to appropriate portions of the system. For instance, the system can include temperature sensors that function to protect the system and/or to provide contextual data that can be processed, with other biometric signals, to analyze health states of the user. If the temperature is too low or too high for safe and effective operation, the system can power off or send warning message to a display (e.g., such as display 670 shown in FIG. 6). A light sensor can function to adjust the brightness of a display such that the display is visible in different background lighting. The system may also include a moisture sensor to evaluate the humidity. The moisture, temperature and other environmental signals can be evaluated and interpreted to relate the environmental context data to the user data.

1.5 System—Assembly

The system 100 of FIGS. 1A and 1B can be assembled according to one or more of embodiments. FIGS. 7A-7C and FIGS. 8A-8H described below illustrate the assembly of one embodiment of the system 100. Alternatively, the system 100 can be assembled in any suitable manner.

As described briefly above, FIG. 7A is a cross section view of a portion of an embodiment of a system. FIG. 7B is an isometric view of a cross section of an expanded portion of the embodiment of the system shown in FIG. 7A, from a top right view. A broad surface of a conductive layer 730 is coupled to a substrate 720 which is coupled to a base 760. A port 724 is shown to pass through the conductive layer 730, the substrate 720 and the base 760. FIG. 7C is a similar isometric view of a system from a top right view. FIG. 7C includes a fastener 710 inserted into the port 724. The fastener 710 is coupled to an interior region of the substrate 720 and the base 760. As described earlier in relation to FIG. 7A, the fastener 710 and the conductive cap 714 can prevent substances such as water or dust from entering through the port 724. The conductive cap 714 forms a conical sheathing around a region of the fastener 710, allowing for compliance between components.

Figure 8A:
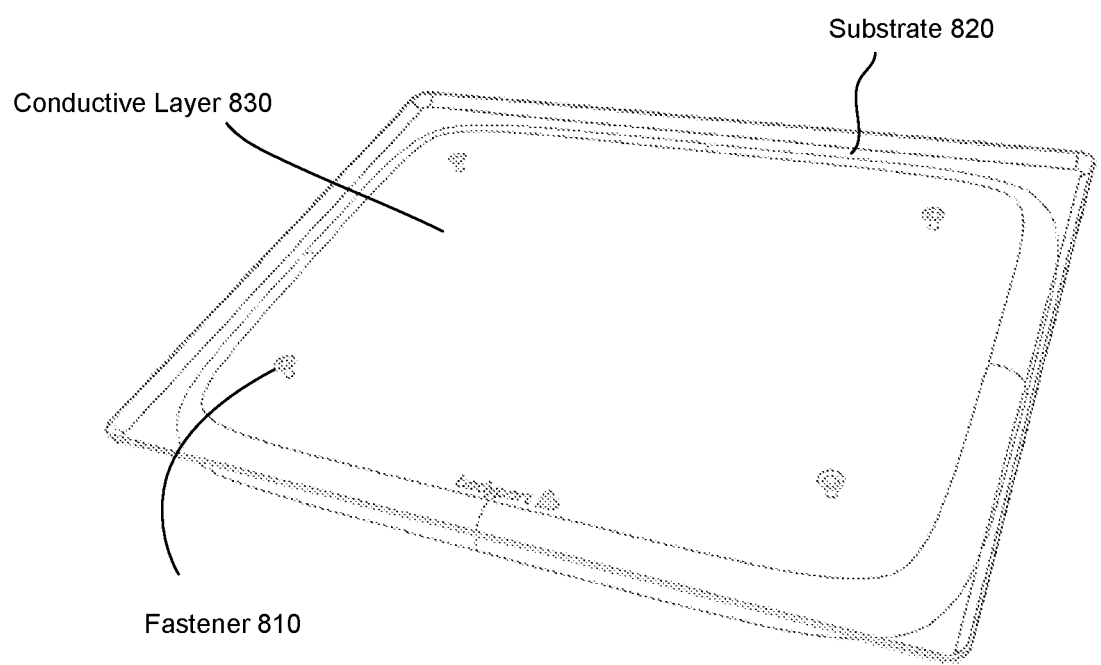
FIG. 8A is an isometric view, from the top right, of an embodiment of a system for health monitoring.

The system components are coupled such that the device can be comfortable and attractive to the user. FIG. 8A is an isometric view, from the top right, of an embodiment of a system described in relation to FIGS. 7B and 7C. The system has a height of 3.1 centimeters, a width of 31.1 centimeters, and a length of 40.6 centimeters. The device can have a length of 20-100 centimeters, width of 10-80 centimeters, and a height of 1-15 centimeters. Alternatively, the system can have any suitable dimensions. The system weighs 7.5 pounds, but the system can have a weight of 2-20 pounds. Alternatively, the system can have a weight of any suitable amount. FIGS. 8B-H show different views of the embodiment shown in FIG. 8A. As such, the dimensions of the system shown in FIGS. 8A-H can be considered consistent for the purposes of illustration.

Figure 8B:
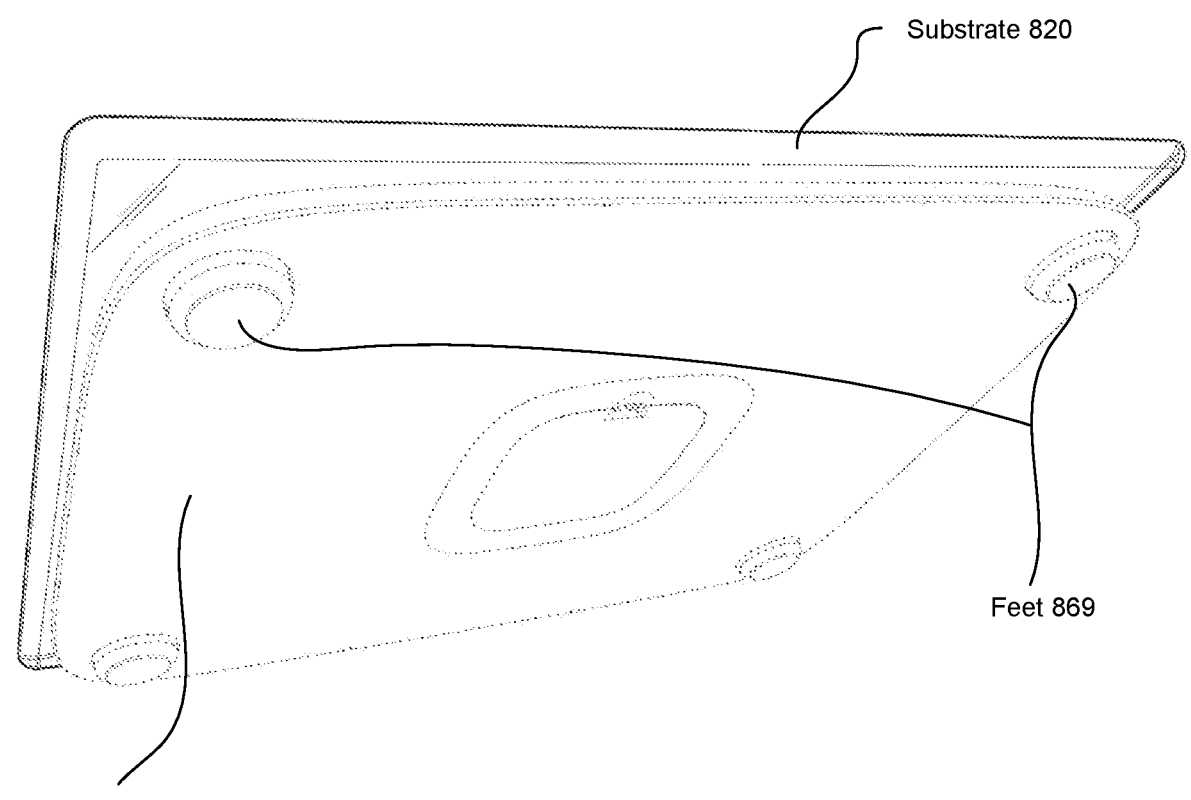
FIG. 8B is an isometric view, from the bottom right, of the embodiment of the system shown in FIG. 8A.

FIG. 8B is an isometric view, from the bottom right, of the embodiment of the system shown in FIG. 8A. The base 860 has an area large enough to provide structural support for the user and the system in various operation modes. Four feet 869 are coupled to or extend from the base 860. The feet 869 provide an interface between the ground and the force sensor(s). Alternatively the base 860 may have two or more feet 869 of various shapes and sizes or may not have feet 869.

Figure 8C:
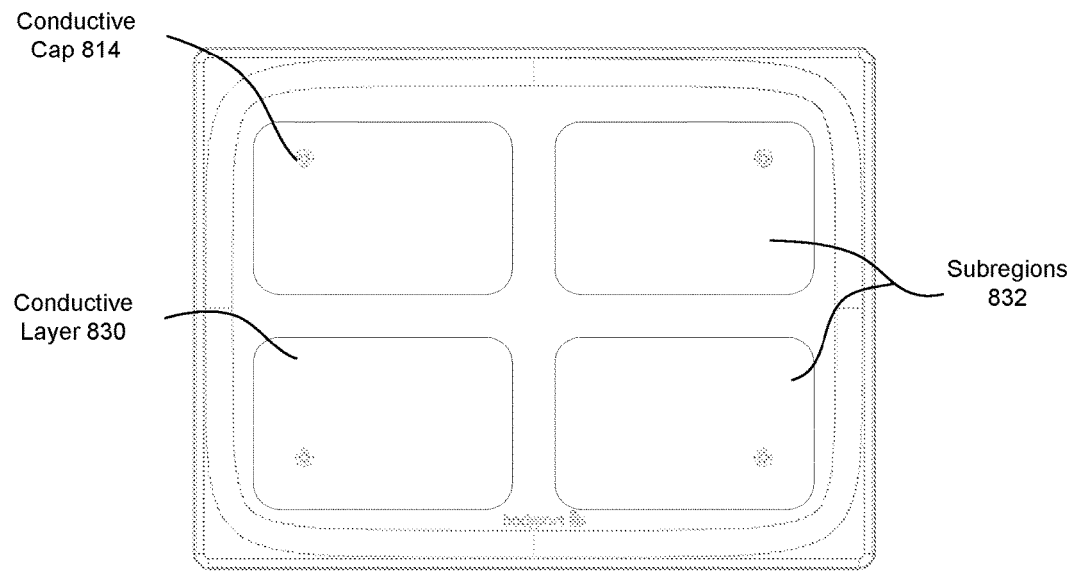
FIG. 8C is a top view of the embodiment of the system shown in FIG. 8A.

FIG. 8C is a top view of the embodiment of the system shown in FIG. 8A. The embodiment includes four conductive caps 814 electrically coupled to the conductive layer 830. The conductive layer includes four electrically isolated subregions 832 illustrated by dashed lines. The conductive layer appears continuous and symmetric to the user across the longitudinal axis to increase aesthetic appeal.

Figure 8D:
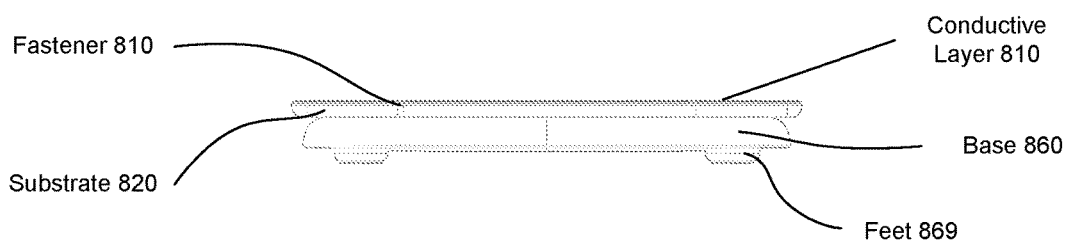
FIG. 8D is a right side view of the embodiment of the system shown in FIG. 8A
Figure 8E:
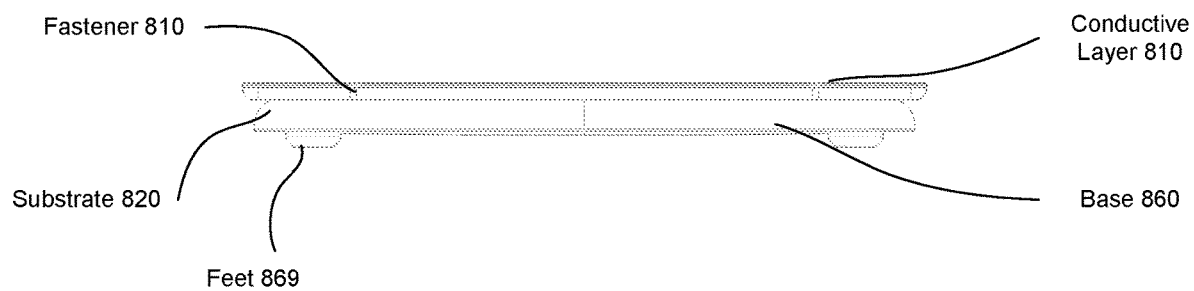
FIG. 8E is a front view of the embodiment of the system shown in FIG. 8A

FIG. 8D is a right side view of the embodiment of the system shown in FIG. 8A. FIG. 8E is a front view of the embodiment of the system shown in FIG. 8A. Shown in FIGS. 8D and 8E, the fastener 810 couples the inferior surface of the conductive layer 810 to the superior surface of the substrate 820. The inferior surface of the substrate 820 is coupled to the superior surface of the base 860. The base includes a front left and right foot 869 and a back left and right leg foot. The feet 869 provide an interface between the base 860 and the ground that provides structural support for the user in various operation modes.

Figure 8F:
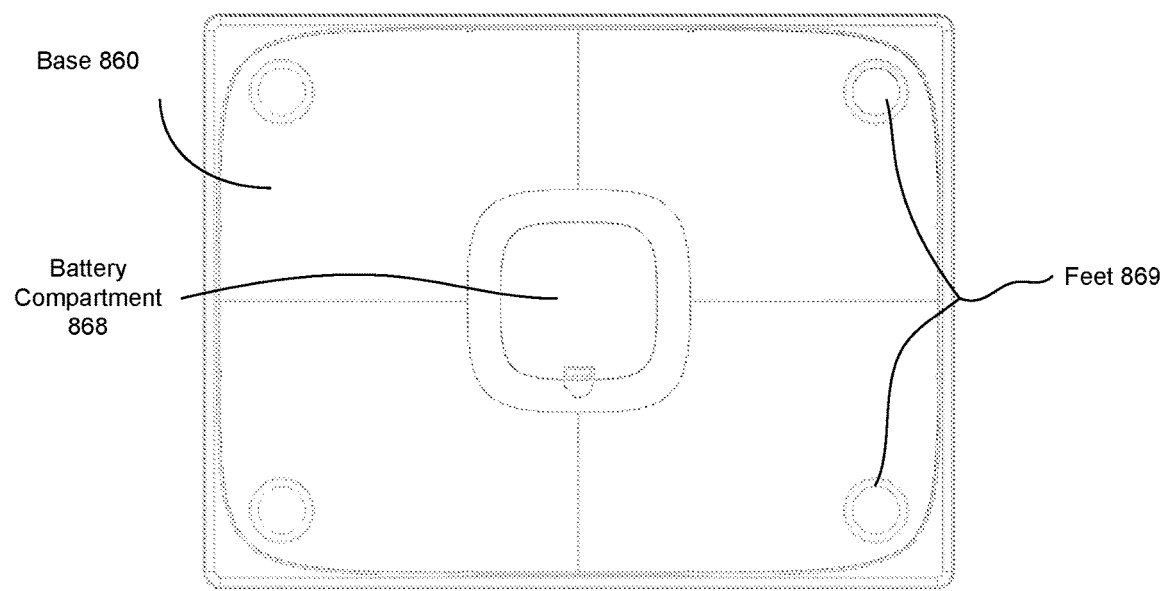
FIG. 8F is a bottom view of the embodiment of the system shown in FIG. 8A

FIG. 8F is a bottom view of the embodiment of the system shown in FIG. 8A. The system is powered by four AA batteries contained in a battery compartment 868 positioned within the base of the system. The battery compartment 868 is located in the center of the bottom of the system. Alternatively, the battery compartment 868 could be located in another region of the system and/or could be coupled to the base 860 or other layer of the system. The system can also be alternatively powered by a rechargeable battery or other form of power through an outlet. FIG. 8F includes four feet 869, a left and right posterior foot 869 and a left and right anterior foot 869. The feet 869 allow the system to be placed on the ground such that the user can stand on the system as directed and the system will remain physically balanced.

Figure 8G:
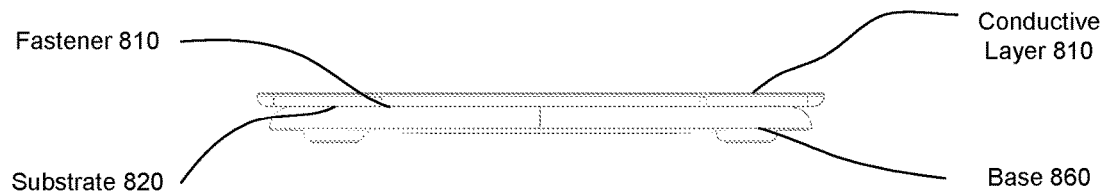
FIG. 8G is a left side view of the embodiment of the system shown in FIG. 8A
Figure 8H:
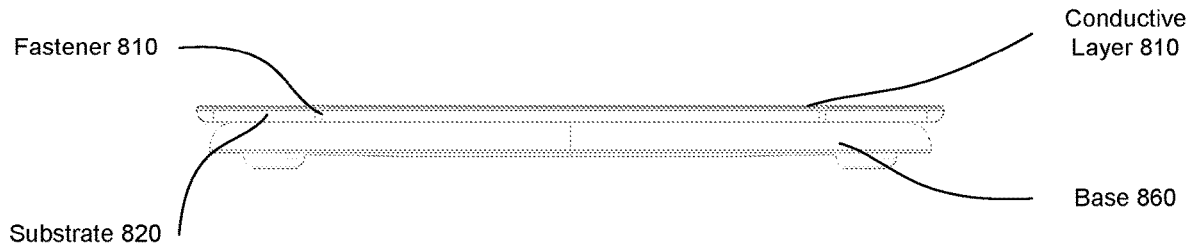
FIG. 8H is a back view of the embodiment of the system shown in FIG. 8A

FIG. 8G is a left side view of the embodiment of the system shown in FIG. 8A and FIG. 8H is a back view of the embodiment of the system shown in FIG. 8A. According to FIGS. 8G and 8H, a fastener 810 couples the inferior surface of the conductive layer 810 to the superior surface of the substrate 820. The inferior surface of the substrate 820 is coupled to the superior surface of the base 860. The base includes a front left and right foot 869 and a back left and right foot 869. The feet 869 provide an interface between the base 860 and the ground that provides structural support for the user in various operation modes.

1.6 System—Operation Modes

Figure 9:
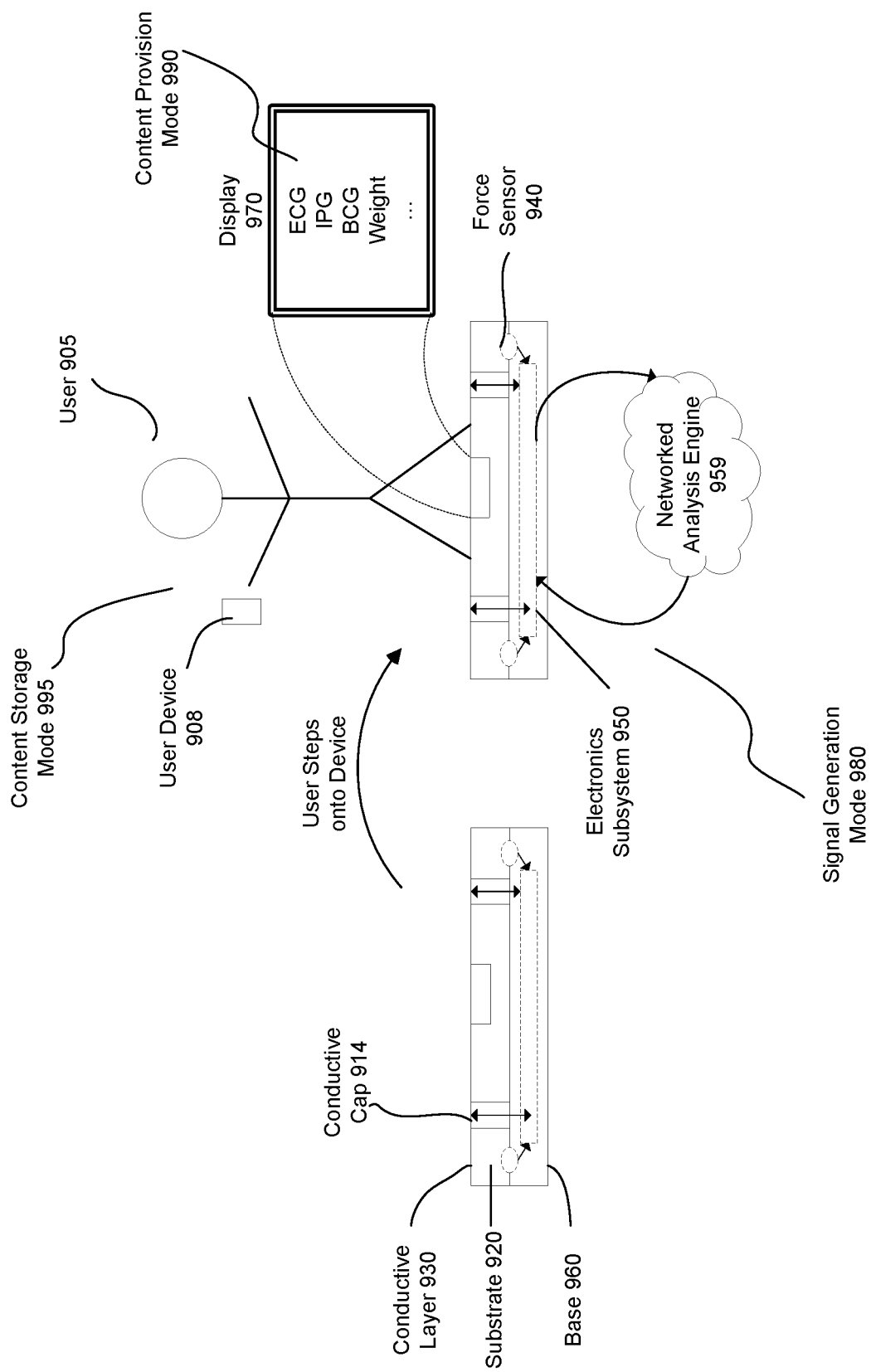
FIG. 9 depicts operation modes of a system for health monitoring, in accordance with one or more embodiments.

There are several operation modes associated with the system 100. FIG. 9 illustrates operation modes of a system for health monitoring, in accordance with one or more embodiments. FIG. 9 includes three modes of the system: a signal generation mode 980, a content provision mode 990, and a content storage mode 995. The system operates in the signal generation mode 980 when the user 905 interacts with the system. The user interface, in the signal generation mode 980, includes a conductive layer 930, a conductive cap 914, a base 960 and a substrate 920. In relation to the signal generation mode 980, when the user 905 steps onto the device, the conductive layer 930 facilitates formation of an electrical circuit through the body of the user, and receives bioelectrical signals from the user 905. The conductive cap 914 transmits the signal to the electronics subsystem 950. A set of force sensors 940 receive a force signal from the interaction and transmit the signal to the electronics subsystem 950.

The electrical signal and force signal received by the electronics subsystem 950 are processed in the signal generation mode 980 by the networked analysis engine 959. The data interpreted by the networked analysis engine 959 can include pulse rate, heart rate variability (HRV), body impedance, and cardiac waveforms (e.g. plethysmograph (IPG), ballistocardiograph (BCG), electrocardiograph (ECG)). The networked analysis engine 959 can determine systolic time intervals such as pulse transit time (PTT), pre-ejection period (PEP), pulse arrival time (PAT), and left ventricular ejection time (LVET) from the cardiac waveforms. The non-cardiovascular metrics from the force sensors evaluated by the networked analysis engine 959 can include body weight and balance analysis. The networked analysis engine 959 can also process and evaluate environmental context data described above.

In the content provision mode 990, as shown in FIG. 9, data interpreted by the networked analysis engine 959 is transmitted to the electronics subsystem, which generates instructions for rendering information derived from outputs of the networked analysis engine 959 at the display. In the content provision mode 990, the display 970, being electrically coupled to the electronics subsystem 950, renders information derived from data processed by the networked analysis engine 959 such as plethysmograph (IPG), a ballistocardiograph (BCG), an electrocardiograph (ECG), weight, and pulse. In the signal generation mode 980, the networked analysis engine 959 can also be in communication with a user device 908 in order to store the data in a content storage mode 995. The user can access his/her data in order to track changes in user health and promote early detection of health related issues.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, one implementation of which is set forth in the following claims.

What is claimed is:

1. A system for measuring health signals for a user, the system comprising:
   a first fastener and a second fastener, each of the first fastener and the second fastener comprising a body and a conductive cap ensheathing a first end region of the body;
   a substrate comprising a first surface, the substrate comprising a first port and a second port each passing into the first surface, the first port retaining the first fastener in position and the second port retaining the second fastener in position;
   a conductive layer coupled to the first surface and separated into a first subregion electrically coupled to the conductive cap of the first fastener and a second subregion electrically coupled to the conductive cap of the second fastener, the first subregion electrically isolated from the second subregion;

a set of force sensors in communication with the substrate; and an electronics subsystem housed by a base and comprising an electrical signal channel electrically coupled to the first fastener and the second fastener and comprising a force signal channel coupled to the set of force sensors, wherein the first fastener secures the substrate between the base and the conductive layer by directly contacting the first subregion of the conductive layer with the conductive cap of the first fastener, passing completely through the substrate via the first port, and attaching to the base by the body of the first fastener, and wherein the second fastener secures the substrate between the base and the conductive layer by directly contacting the second subregion of the conductive layer with the conductive cap of the second fastener, passing completely through the substrate via the second port, and attaching to the base by the body of the second fastener.

2. The system of claim 1, wherein the conductive cap of at least one of the first fastener and the second fastener is flush with the conductive layer.

3. The system of claim 1, wherein the body of at least one of the first fastener and the second fastener is composed of a conductive metal material and wherein the conductive cap of at least one of the first fastener and the second fastener is composed of an electrically conductive polymer.

4. The system of claim 3, wherein the electrically conductive polymer, with at least one of the conductive layer and the substrate forms a seal that prevents fluid flow toward the electronics subsystem during use.

5. The system of claim 3, wherein the electrically conductive polymer comprises of carbon-doped silicone rubber.

6. The system of claim 1, wherein the conductive cap of each of the first fastener and the second fastener comprises a compliant material, wherein the conductive cap of the first fastener is configured to provide a mechanical interface between the first fastener, the substrate, and wherein the conductive cap of the second fastener is configured to provide a mechanical interface between the second fastener, the substrate, and the base housing the electronics subsystem.

7. The system of claim 1, further comprising a retainer, wherein a second end region of at least one of the first fastener and the second fastener, with the retainer, couples the substrate to the base.

8. The system of claim 7, further comprising a conductive lead coupled to at least one of the first fastener and the second fastener by the retainer, the conductive lead electronically coupled to the electronics subsystem.

9. The system of claim 8, wherein the base comprises an internal cavity, wherein at least one of the first fastener and the second fastener, with the retainer, retains the conductive lead in position within the internal cavity, and wherein the electronics subsystem is secured to the base within the internal cavity.

10. The system of claim 1, wherein the electronics subsystem comprises a signal generation mode wherein, in response to a user interaction with the conductive layer, the first and the second fasteners detect an electrocardiogram (ECG) signal contemporaneously with generation of a force signal by the set of force sensors.

11. The system of claim 10, further comprising a display coupled to the electronics subsystem, the electronics subsystem comprising a content provision mode wherein, in response to the user interaction, the electronics subsystem provides information derived from the ECG signal and the force signal through the display.

12. The system of claim 11, wherein the display is positioned inferior to the first surface of the substrate and the substrate, with the conductive layer, allows passage of light from the display.

13. A system for measuring health signals, the system comprising:

a first fastener and a second fastener, each of the first fastener and the second fastener comprising a body and a conductive cap coupled to a first end region of the body;

a substrate comprising a first surface, the substrate comprising a first port and a second port each passing into the first surface, the first port retaining the first fastener in position and the second port retaining the second fastener in position;

a conductive layer coupled to the first surface and coupled to the conductive caps of the first fastener and the second fastener; and a base coupled to the substrate by the first fastener and the second fastener, wherein the first fastener secures the substrate between the base and the conductive layer by directly contacting the conductive layer with the conductive cap of the first fastener, passing completely through the substrate via the first port, and attaching to the base by the body of the first fastener, and wherein the second fastener secures the substrate between the base and the conductive layer by directly contacting the conductive layer with the conductive cap of the second fastener, passing completely through the substrate via the second port, and attaching to the base by the body of the second fastener.

14. The system of claim 13, wherein the conductive cap of each of the first fastener and the second fastener is flush with the first surface of the substrate, wherein the conductive cap of the first fastener, with at least one of the conductive layer and the substrate, forms a seal that prevents fluid flow past the body of the first fastener, and wherein the conductive cap of the second fastener, with at least one of the conductive layer and the substrate, forms a seal that prevents fluid flow past the body of the second fastener.

15. The system of claim 13, wherein the body of at least one of the first fastener and the second fastener is composed of a conductive metal material and wherein the conductive cap of at least one of the first fastener and the second fastener is composed of an electrically conductive polymer.

16. The system of claim 13, further comprising a first retainer coupling a second end region of the first fastener to the base and a second retainer coupling a second end region of the second fastener to the base.

17. The system of claim 13, further comprising an electronics subsystem retained within an internal cavity of the base, a first conductive lead coupled to the first fastener by a first retainer, and a second conductive lead coupled to the second fastener by a second retainer, the first conductive lead and the second conductive lead coupled to an electrocardiogram (ECG) channel of the electronics subsystem.

18. The system of claim 17, further comprising a display coupled to the electronics subsystem, the electronics subsystem comprising a content provision mode wherein, in response to a user interaction with the conductive layer, the electronics subsystem provides information derived from an ECG signal received at the ECG channel.

19. The system of claim 13, further comprising an electronics subsystem and a set of force sensors along a force transmission pathway from the substrate to the base, wherein the set of force sensors is electronically coupled to a force signal channel of the electronics subsystem.

20. The system of claim 19, wherein the electronics subsystem comprises a signal generation mode wherein, in response to a user interaction with the conductive layer, the first and the second fasteners detect an electrocardiogram (ECG) signal contemporaneously with generation of a force signal by the set of force sensors.

\* \* \* \* \*